United States Patent [19]

Vorys

[11] 4,291,028

[45] Sep. 22, 1981

[54] FOLLICULAR PHASE ESTROGEN OR PROGESTIN WITH PHYSIOLOGIC ESTROGEN/PROGESTIN LUTEAL PHASE REPLACEMENT DRUG DELIVERY SYSTEM

[76] Inventor: Nichols Vorys, 336 S. Columbia Ave., Columbus, Ohio 43209

[21] Appl. No.: 83,636

[22] Filed: Oct. 11, 1979

Related U.S. Application Data

[63] Continuation of Ser. No. 865,851, Dec. 30, 1977, abandoned.

[51] Int. Cl.$^3$ .............................................. A61K 31/56
[52] U.S. Cl. ................................... 424/238; 424/241; 424/243
[58] Field of Search ........................ 424/238, 241, 243

[56] References Cited

U.S. PATENT DOCUMENTS 3,969,502  7/1976  Lachnit-Faxson .................. 424/241
4,066,757  1/1978  Pasquale ............................. 424/241

Primary Examiner—Elbert L. Roberts
Attorney, Agent, or Firm—Kenyon & Kenyon

[57] ABSTRACT

A method, formulation, and steroid drug delivery system for the administration of sex steroids for menstrual cycle regulation is disclosed. The invention is useful in clinical applications for pregnancy spacing and treatment of menstrual dysfunction. Progestin and estrogen are administered in a treatment cycle mimicking sex steroid hormones in the normal menstrual cycle. The steroid treatment cycle is divided into arbitrary and discrete follicular and luteal phase segments beginning with the onset of menstruation. In the early segment of the follicular phase no exogenous steroid is administered. Depending on the clinical and/or physiologic situation of a patient, unopposed progestin or estrogen is then administered. In the preferred embodiment an early luteal phase follows with low dose administration of combination estrogen/progestin; mid luteal estrogen and progestin is administered in a dose adequate to suppress pituitary FSH and LH and to maintain the endometrium; and terminally, a reduced dosage of combination estrogen/progestin is administered. The clinical success of the method and formulation depends not only upon the biologic potency of the progestin molecule administered but also depends upon the dose and temporal relationship of administration of exogenous estrogen, progestin, and combination estrogen/progestin. As a consequence, any FDA approved synthetic estrogen or progestin, in pharmacologically appropriate dosage is suitable for formulation in accordance with the present invention. Menstrual cycle regulation and effective contraception is achieved by hypothalamic-pituitary dysrhythmia rather than sustained FSH, LH, endogenous estrogen suppression. A reduced exposure to the adverse endocrine and metabolic effects of high dose estrogen and progestin administered concurrently is accomplished. Upon discontinuation of the administration of the present invention, prompt FSH and subsequent LH recovery ensue, providing for an appropriate return of ovulation and appropriate menstruation in the prior to drug normal ovulating patient. The method and formulation further allow the physician to take physiologic corrective measures in menstrual dysfunction patients who may or may not seek contraception and present as hypoestrogen, euestrogen, or hyperestrogen ovulation dysfunction or anovulatory.

9 Claims, 11 Drawing Figures

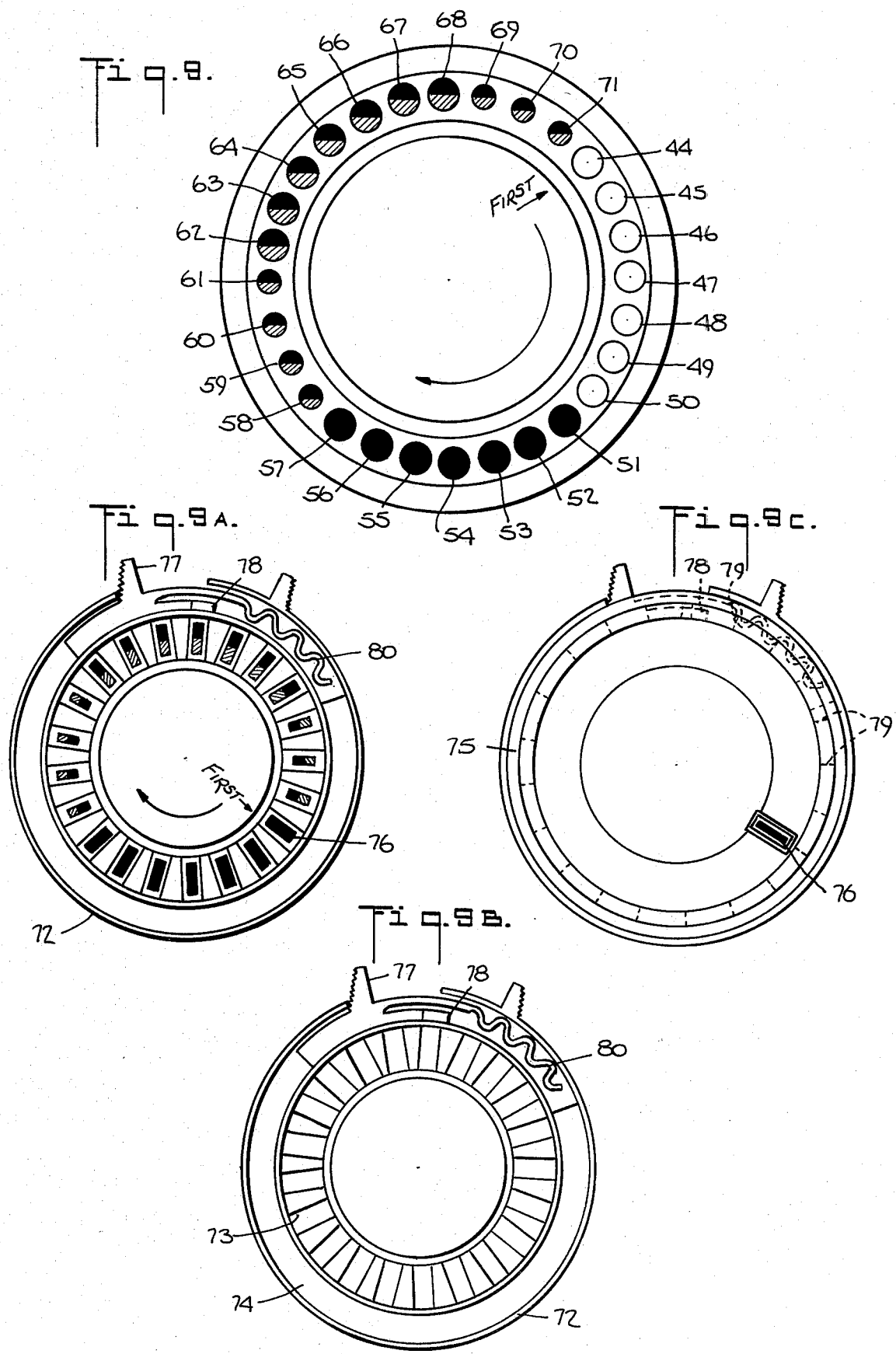

FOLLICULAR PHASE ESTROGEN OR PROGESTIN WITH PHYSIOLOGIC ESTROGEN/PROGESTIN LUTEAL PHASE REPLACEMENT DRUG DELIVERY SYSTEM

This is a continuation of application Ser. No. 865,851 filed Dec. 30, 1977, now abandoned.

BACKGROUND OF THE INVENTION

The following specification describes my invention of a new steroid drug delivery system. The invention is a new method and formulation useful for menstrual cycle regulation to achieve ovulation control and to treat menstrual dysfunction. More particularly, my invention is a follicular-luteal sex steroid replacement which may be adapted to the specific presenting clinical state of the individual patent. Thus, the method for sex steroid replacement of the invention is useful in the management of clinical states of menstrual irregularity, menstrual dysfunction, ovulation pain, primary dysmenorrhea, and premenstrual tension syndrome. The method is also useful as a sex steroid drug delivery system for pregnancy spacing where sex steroids are widely used today.

Opportunities for undesirable clinical, endocrine and metabolic side effects, which have resulted from exogenous steroid dosages administered in prior art contraceptive methods and formulations are reduced by the present invention. The hepatic, morphologic, metabolic, and endocrine adverse consequences from sex steroid treatment cycles are reduced by steroid administration in accordance with the present invention. Future ovulation disturbance in patients administered sex steroids for menstrual contraception purposes is also minimized.

In addition, the present invention provides a method and formulation for the delivery of steroid drugs which allows a rational decrease of exogenous estrogen in sex steroid menstrual cycle management. The method minimizes both the dose and days of administration of exogenous estrogen and minimizes the days of combination exogenous estrogen and progestin in sex steroid treatment cycles. The invention provides adequate menstrual cycle control and physiologic correction of menstrual dysfunction in diverse clinical problems that no current estrogen/progestin formulation adequately manages in a rational physiologic manner.

PROBLEMS OF THE PRIOR ART

In the prior art, the combination and sequential cyclic administration of sex steroid hormone drugs by oral dosage to achieve contraceptive effects has been known since about 1957.

A recent survey of currently available steroid dosages for oral contraception lists some twenty-four commercially available formulations. (Chart, "Hormone Content of Currently Available Oral Contraceptives", Ross Laboratories, Columbus, Ohio 43216, March 1976). These formulations administer either a "combination" of both estrogen and progestin in tablet form each day for twenty or twenty one days following menstruation or provide a "microdose" tablet of progestin alone in a continuous fashion. Such contraceptive dosages are formulated from synthetic estrogens, mestranol and ethinyl estradiol, and synthetic progestins: norgestrel, norethindrone, norethindrone acetate, ethynodiol diacetate, and norethynodrel. Sequential administration of estrogen and progestin, while previously allowed, has been discontinued because of associated cancer of the endometrium.

The administration of these exogenous sex steroid formulations has been associated with the development of adverse side effects in patients. In 1956, when Rock, Pinkus, et al. began clinical trials of a combined dosage of estrogen and the progestin, 19 nortestosterone, for contraceptive objectives, their study considered only cursory, endocrinologic and metabolic consequences and made only preliminary evaluation of the metabolic fate of the exogenous estrogen and progestin administered. Subsequent authors have, however, reported both mild and serious side effects resulting from combination and sequential oral estrogen and progestin administration. The mild side effects include nausea, vomiting, fatigue, lassitude, weight gain, fluid retention, chloasma, and headache. The more serious side effects were changes in liver function, chloestatic jaundice, thromboembolic disease, alteration in carbohydrate and lipid metabolism, hypertension, modular hyperplasia of the liver and carcinoma of the endometrium.

By 1970, the adverse effects of high level dosages of combination estrogen/progestin contraceptives were more widely reported. Thromboembolic disease was more frequently associated with larger doses of estrogen, i.e., over 0.05 mgm. Other adverse side effects, particularly involving the liver, were also noted: liver tumors or nodular hyperplasia, were invariably associated with high dose estrogen/progestin administration for long periods of time (two years or more); liver protein synthesis was affected by exogenous estrogen, increasing the serum proteins: transcortin, thyroid binding globulin, TE binding globulin, transfuren, ceruloplasmin, pre-beta lipoproteins, beta lipoproteins, angiotensinogen, IGg, 2 macroglobulen, and prothrombin related coagulation factors, i.e., VII, X, and probably II, VIII, and IX.

To reduce adverse metabolic and endocrine consequences, work in the prior art sought to decrease the dosage of both the estrogen and progestin component of the combination sex steroid birth control pill. For example, the pill combining the progestin, norethynodrel, and the estrogen, mestranol, first introduced in 1957, was subsequently redesigned with a lower progestin and estrogen content in 1960 and 1964. Norethindrone, a 19-nortestosterone progestin, was introduced in 1963 and combined with the estrogen, mestranol. Dosage levels of the pill combining these steroids were reduced in 1963, 1967 and 1975.

The later identification of more biologically potent progestin molecules allowed the prior art to reduce the dosage of synthetic progestin and/or estrogen used in combination birth control pills. Thus, when, norgestrel and ethinyldiol diacetate, both potent progestins, were respectively introduced in 1968 and 1969, combination pills formulated with these progestin allowed a reduced dosage of progestin and/or estrogen. As more biologically potent progestins were identified, the progestins were not only administered in a lower daily dosage but also allowed a reduced dosage of the concurrently-administered synthetic estrogen. Also, in accordance with the estrogen reduction approach of the prior art, 19-nortestosterone compounds, such as norethynodrel and ethinyldiol diacetate were identified, which not only acted as oral progestin but also had some associated inherent estrogen activity. Other substitute oral progestins have increased androgen activity and maximum anti-estrogen activity. The most potent 19 nortestoserone progestin is norgestrel, which is significantly more pharmacologically potent than norethindrone, which because of its biologic potency, allowed the formulation of a low dose combination pill (marketed under the trademark "Lo/Ovral") with a daily estrogen dose reduced to under 0.05 mgm., and finally to as low as 0.03 mgm., for twenty-one days in daily combination with a reduced progestin dosage. No progestin, other than norgestrel, can be administered in comparable low pharmacologic doses of progestin and estrogen without serious menstrual disarray and exceedingly poor continuation rates.

Of the prior art combination pills, many reproduction endocrinologists consider Lo/Oral the safest pill from a metabolic and endocrine standpoint.

Weaker progestins such as northindrone and norethindrone acetate were also formulated with low dose estrogen in combination pills. These latter formulations, in several dose levels, however, were associated with breakthrough bleeding and unpredictable uterine bleeding in 40 to 50% of the cases. Because of this clinical fact, their acceptance has been minimal.

Hence, because of the prior art approach in developing new and more potent steroid molecules, a principal characteristic of the various combination contraceptive steroid formulations in the market today is that the design of each is predicated on the potency of the progestin molecule used in the combination with its inherent ability to allow a reduced dosage of estrogen. To wit, the more potent the progestin administered, less estrogen in combination with the progestin is required to achieve effective contraception and menstrual cycle control. However, when a less potent progestin is administered in combination with a reduced dosage of estrogen to adapt to adverse metabolic effects, menstrual cycle disruption results. Of the lower dose combination pills, Lo/Ovral, combining norgestrel, 0.3 mgm., with a low dose ethinyl estradiol, 0.03 mgm., for twenty-one days has the best overall performance characteristics. This formulation, as does all other combination pills, however, provides a uniform and unremitting dosage of exogenous estrogen in combination with progestin during the twenty-one day drug cycle, a pharmacological principle which is contraphysiologic for the management of menstrual dysfunction.

The prior art also unsuccessfully attempted a sequential administration of estrogen and progestin steroids. In about 1967, several drug companies marketed an "estrogen sequential" formulation which provided for a cycle dosage of sixteen days of unopposed estrogen, followed by five or seven days of combination estrogen and progestin. A group of clinical and metabolic side effects characteristic of estrogen sequential developed as a result of the large dose of unopposed exogenous estrogen administered by this formulation. The adverse effects included leukorrhea, fluid retention, weight gain, escape ovulation, and unexpected pregnancies. Recently, estrogen sequential has been reported to be associated with abnormal morphology of the endometrium, suggesting premalignant lesions and carcinoma of the endometrium. Because of such side effects, estrogen sequential formulations have been removed from the market.

In these steroid dosage formulations of combined estrogen and progestin, it is believed that the large dose estrogen component of the combination and estrogen sequential pill, when given for sustained periods of time, because of the enterohepatic circulation of estrogen, provides little metabolic rest from exogenous estrogen and results in an altered protein synthesis by the liver. This affects metabolic consequences in carbohydrate metabolism (decreased glucose tolerance test), hypertension (increased angiotensinogen), and lipid metabolism, i.e., elevation of cholesterol in Fredrickson Class IIa and triglycerides in Fredrickson Class IV hyperlipidemias.

Concurrent progestin administration affects target cell membrane permeability. Exogenous estrogen in combination with progestin is transported into the cell to the cytosol estrogen receptor site at a greater rate and concentration, thus estrogen in the presence of progestin has a more profound effect on liver cell protein synthesis and cell replication. Thus, in the combination birth control pills, where estrogen is administered concurrently with progestin, there results an unremitting abnormal synthesis of proteins by the liver as well as alteration in the excretory capabilities of the liver.

Another approach to prevent the endocrine and metabolic abnormalities associated with combination dosage of estrogen/progestin employed progestin solely. One such method was a long-lasting injectible delivery system which, however, resulted in side effects including the development of abnormal follicular and corpus luteum phases of the menstrual cycle and unpredictable bleeding. Another progestin method, provides a low dose of progestin in the form of the "mini-pill", which acts on the cervix and lower tract to prevent pregnancy. Small continued "microdoses" of several progestins, particularly norethindrone and norgestrel, were attempted in this manner; but each has been associated with breakthrough bleeding and abnormal follicular and corpus luteum phases of the menstrual cycle. The fate of the corpus luteum in patients administered the mini-pill is in one-third of the patients normal in function; and in one-third, abnormal, and in the remaining third, absent.

While the solo dosage of progestin reduced estrogen dependent side effects of contraceptive pills, the method was associated with menstrual cycle chaos and severe menstrual derangement. In patients receiving the "mini-pill" it was estimated that breakthrough bleeding occurred in approximately 40 to 50% of the patients and the continuation rate for patients was less than 25% in one year. Thus, progestin alone is unsatisfactory for long term clinical use either as a contraceptive or for menstrual cycle regulation.

In sum, in most instances the prior art neither successfully reduced the estrogen present nor the adverse metabolic consequences associated with oral sex steroid administration for contraception. Rather, each variation produced a new and different set of clinical, endocrine, and metabolic adverse consequences. Out of twenty-four combination estrogen/progestin formulations currently available, reproduction endocrinologists generally agree that only Lo/Ovral closely satisfies the clinical, endocrine, and metabolic need of the oral contraceptive patient. However, this formulation design is inappropriate for menstrual dysfunction patients.

OBJECTIVES OF THE PRESENT INVENTION

The follicular-luteal sex steroid replacement and drug delivery system of the present invention has as its object the reduction of the clinical, endocrinologic and metabolic side effects associated with the administration of sex steroids. Another object is to reduce, not only by amount, but also by the number of days administered during the cycle, the exogenous estrogen administered. This allows maximum target organ rest of hypothalamus, pituitary, and liver from exogenous estrogen. A further object is to reduce the dosage of progestin so that moderately potent biologic progestins may be employed as effectively as the potent progestin, norgestrel. Another object is to reduce the number of days throughout the drug cycle that progestin is administered concomitant with exogenous estrogen. Another objective is to reduce the amount of exogenous estrogen administered with any or all moderately potent synthetic progestins to an irreducibly low concentration while preserving menstrual cycle control.

Thus, the delivery system of the invention minimizes the undesirable clinical, endocrine, and metabolic adverse consequences associated with the administration of high dose exogenous estrogen for too many consecutive days each treatment cycle and increases the target organ estrogen recovery period after each treatment cycle which is far too short in the prior art combination dosage cycles.

The present invention also provides a new sex steroid formulation for therapeutic menstrual cycle regulation which permits a prompt return to ovulation; reduces both the amount of and length of time during which exogenous estrogen is administered during the drug cycle; reduces the length of time exogenous estrogen and progestin are administered together during the drug cycle; lengthens the end organ and cellular recovery period from exogenous estrogen; minimizes hypothalamic and pituitary sustained supression; relies on CNS, i.e., hypothalamus and pituitary dysrhythmia of gonadotropins release, rather than total sustained suppression during the follicular phase of the drug cycle; minimizes the dose and the length of time of synthetic progestin administration; uses adequate amounts of exogenous synthetic estrogen and progestin to suppress endogenous FSH and LH for approximately seven days during the corpus luteum phase of the drug cycle; administers exogenous synthetic estrogen or progestin to create an arbitrary follicular phase and estrogen/progestin to create a corpus luteum phase in the treatment cycle with adequate but not excessive exogenous estrogen and progestin to maintain the integrity of the endometrium. Further, the present invention does not excessively suppress gonadotropins as results with present sex steroid oral dosage formulations and provides more pharmacologic flexibility.

Hence, the drug dosage system and treatment method of the present invention accomplishes its therapeutic objectives as set forth above through various embodiments which may be more particularly adapted for the hypoestrogen, euestrogen and hyperestrogen clinical states of the presenting patient. Depending upon such clinical state, the appropriate sex steroid delivery system in accordance with the invention is selected for therapeutic administration for treatment, management and regulation of the menstrual cycle. Further, unlike the combination estrogen and progestin sex steroids delivered by the prior art, the present invention is useful in the correction of hypothalmic-pituitary physiology of menstrual dysfunction and its clinical manifestations.

Thus, in addition to pregnancy spacing and oral steroid contraception uses, for the euestrogen and hyperestrogen presenting clinical states, the method and formulation of the invention is useful for the treatment of menstrual irregularity, as for example, menorrhagia, hypermenorrhea, menometrorrhagia, oligomehorrhea; 2° amenorrhea (in presence of progesterone withdrawal—Prolution 100 mgm I.M.); dysmenorrhea, premenstrual tension; and for ovulation pain. For the euestrogen and hyperestrogen clinical states in which the follicular-luteal drug delivery and steroid supplementation system of the invention is applied for contraception, when done on a long term basis the contraceptive application of the invention minimizes the adverse endocrine and metabolic effects of excessive exogenous estrogen or estrogen administered in combination with progestin (allowing for increased concentration of estrogen at the end organ cytosol receptor) as compared to the prior art combination estrogen/progestin oral contraception dosage systems.

For treatment of and/or sex steroid delivery to patients in the hypoestrogen presenting state, the present invention provides a sex steroid replacement and/or supplementation drug delivery system for such clinical states as 1° and ammenorrhea, 2° amenorrhea, hypomenorrhea, oral contraception breakthrough bleeding secondary to inappropriate ratios of exogenous estrogen/progestin or due to inadequate unopposed estrogen priming, and minimizes escape endogenous estrogen and its subsequent withdrawal during the cycles of progestin only and low dose contraceptive steroid administration as is seen with prior art combination oral estrogen/progestin and their current modifications.

The present invention is dependent more upon the temporal relationship of exogenous steroids administered to the endogenous hormones of the patient's presenting clinical state and to interrelationships of the exogenous steroids throughout the steroid administration cycle than to the absolute potency of the particular sex steroid administered. Hence, any synthetic estrogen and progestin can be used in accordance with the invention if the temporal interrelationships, relative dose, duration of administration, and ratio of exogenous estrogen and/or progestin are approximately biologically equivalent to examples, and variations thereof, of the invention as hereinafter set forth. The invention may be adapted to be employed with either currently FDA approved synthetic estrogen: mestranol and ethinyl estradiol; and any of the FDA approved synthetic progestins: norgestrel, norethindrone, norethindrone acetate, ethynodiol diocetate and norethynodrel.

In contrast to prior art steroid dosage formulations which administer a uniform daily dose of combined exogenous steroids throughout the drug administration cycle, the present invention separately treats discrete segments of a presenting patient's mentrual cycle, and, accordingly, provides a drug administration cycle likewise having discrete exogenous steroid characteristics which are temporally related to the presenting cycle. Thus, an arbitrary steroid administration cycle superimposes exogenously delivered dosages over the endogenous hormone characteristic of the presenting menstrual cycle. The invention provides a separate arbitrary steroid characteristic for the follicular and corpus luteum phases of the menstrual cycle. Hence, in the invention an arbitrary follicular steroid phase and an arbitrary luteal steroid phase comprise a sex steroid drug administration cycle. In turn, each phase, i.e. follicular and luteal may itself have discrete segments with distinct steroid characteristics.

The first half of the invention's arbitrary follicular phase rests the end organs; hypothalamus, pituitary, endometrium, and liver from both estrogen and progestin. The second half of the arbitrary follicular phase exposes hypothalamic releasing hormone and the pituocyte to primary doses (depending on the presenting clinical state) of exogenous estrogen or small doses of exogenous progestin, but never to estrogen/progestin together. Endogenously, estrogen and progestin are seen only in the normal follicular phase about one day prior to ovulation. The corpus luteum phase in the treatment cycle increases dosage of combined estrogen/progestin gradually in its early stage, but requires adequate exogenous estrogen and progestin in its middle stage to suppress pituitary FSH and LH and to maintain the integrity of the endometrium. The terminal portion of the corpus luteum phase may reduce the dose of combination estrogen/progestin to allow for FSH, LH recovery and initiate prompt endometrial withdrawal bleeding upon cessation of the steroid administered in one drug cycle.

Because the invention establishes a separate and distinct steroid administration characteristic for each of a follicular and luteal phase of an arbitrary steroid administration cycle, the administration cycle can be adapted to either the hypoestrogen, euestrogen or hyperestrogen clinical presenting patient by the administration of either unopposed estrogen or progestin during the second half of the follicular phase. In its preferred embodiment, the arbitrary corpus luteum retains a fixed ratio of estrogen/progestin: first, low dose; then FSH, LH suppressive doses, as well as endometrial maintenance doses, and, finally, a terminal decrease of estrogen/progestin. The arbitrary corpus luteum (about fourteen days) of the steroid administration cycle is designed for proper endometrium maturation and predictable menstrual function just as is seen in the ovulatory menstrual cycle.

Thus, the present invention provides a treatment method and steroid drug delivery system minimizing the dose and days of administration of exogenous estrogen in oral sex steroid treatment cycles; minimizing the days of combination exogenous estrogen and progestin in oral sex steroid treatment cycles; minimizing hepatic, morphologic distortion, metabolic, and endocrine adverse consequences from oral sex steroid treatment cycles; and minimizing future ovulation disturbance in patients administered oral sex steroids for menstrual cycle dysfunction. In addition, the present invention is a method for sex steroid oral replacement in the management of menstrual irregularity; method for oral sex steroid replacement in the management of menstrual dysfunction, i.e., hypermenorrhea, menorrhagia, primary amenorrhea, 2° amenorrhea, oligomenonhea, ovulation pains, primary dysmenorrhea; and a method for oral sex steroid replacement in pregnancy spacing.

BRIEF DESCRIPTION OF THE DRAWINGS

In FIG. 2, the estrogen level is depicted against a background of FSH and LH levels for comparison through one ovulatory menstrual cycle. The cycle is divided into preovulatory (follicular) and post-ovulatory (corpus luteum) segments, divided by the LH peak at which ovulation occurs. The occurrence of menses and days of the cycle and their relationship with ovulation and menstruation are indicated as the axis against which the ranges of FSH, LH and estrogen are plotted.

Also in comparison with examples of the present invention and the endogenous estrogen distribution, FIG. 5 depicts several prior art dosage formulations of steroid contraceptives, including the daily dosage level and distribution through the cycle of combination formulations, the progestin alone "mini-pill", and the now defunct estrogen sequential.

FIGS. 9 and 9A–9C depict a tablet package for the oral administration of steriod tablets during a drug administration cycle of the follicular luteal replacement formulations of the invention. Daily tablets are formulated and assembled in a unitary package dispenser such as the one depicted for orderly administration in daily dosage and interrelationships in accordance with the invention.

DESCRIPTION OF PREFERRED EMBODIMENTS

Figure 1:
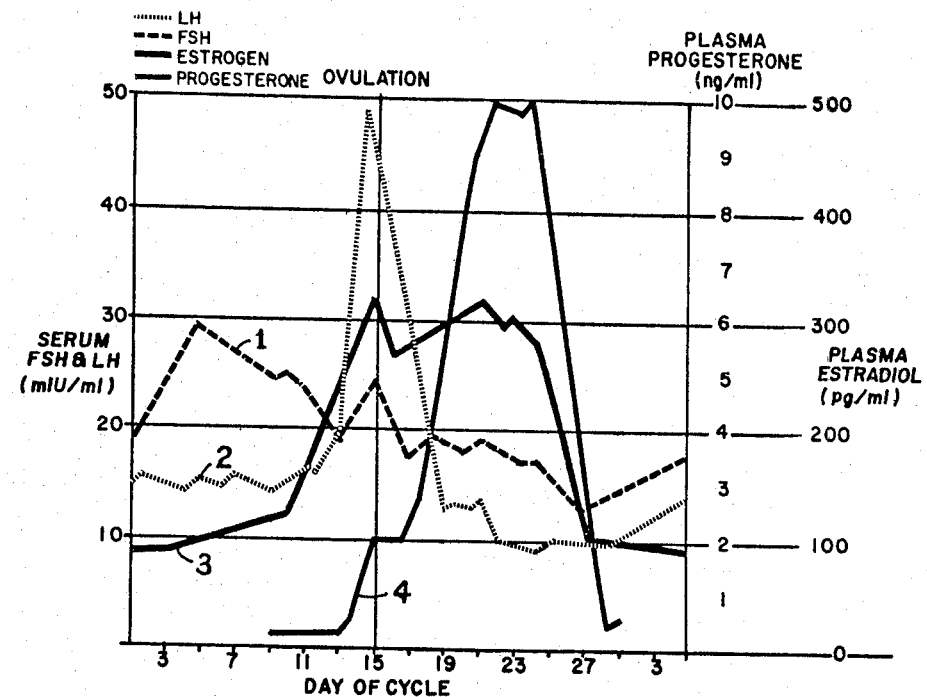
FIG. 1 depicts the blood levels and relationships in a normal ovulatory menstrual cycle of LH, FSH, estradiol 17B, and progesterone as measured by radioimmunoassay in a patient receiving no exogenous steroids.

In accordance with the present invention, pharmacologic overdoses of combination synthetic estrogen/progestin, which are associated with the adverse side effects produced by the exogenous hormone administration of prior art systems, are substantially reduced. In contrast to the contraphysiologic administration of an unremitting daily dosage of exogenous estrogen and progestin and nominal inadequate rest periods to the end organs from exogenous steroids characteristic of the prior art, the follicular-luteal replacement system mimicks the hormone levels of the natural ovulation cycle by providing an exogenous dosage of synthetic estrogen and progestin analogous to the relationship of estrogen and progesterone which is elaborated in the normal ovulatory menstrual cycle.

Further, no prior art dosage system preserves as does the present invention, the independent functions and physiologic necessity of the follicular and corpus luteum stages in a menstrual cycle of a patient treated with exogenous sex steroids.

Nor does any prior art dosage system rest or provide recovery time for the hypothalamus, pituitary, or endometrium during the follicular phase, as allowed by the present invention's arbitrary follicular phase of the treatment cycle, nor allow for monthly partial recovery from exogenous sex steroid suppression. Nor do prior art systems stimulate FSH subsequent to cessation of the previous treatment cycles.

Such is accomplished by terminal reduction of estrogen/progestin in the previous treatment cycle, no exogenous sex steroids in the first seven days of the follicular phase of the treatment cycle and either unopposed progestin or estrogen in the second half of the follicular phase of the treatment cycle.

Further the invention's follicular phase design provides for endometrial priming either due to exogenous estrogen in the second half of the follicular phase and/or to stimulate endogenous estrogen.

In the present invention, the physiologic relationship and the pharmacologic activity of estrogen or progestin are preserved independently in an arbitrary follicular phase of the treatment cycle. The arbitrary corpus luteal phase imposed on the treatment cycle recognizes the pharmacologic advantage of a graduated increase of low dose exogenous combination estrogen/progestin in the arbitrary corpus luteum and the desirability of scheduled predictable FSH and LH suppression for a short time frame (seven to ten days) followed by a short term terminal reduction of estrogen/progestin in the arbitrary corpus luteum steroid administration phase. No prior art system has a standarized physiologically designed corpus luteum preceded by no exogenous estrogen or progestin from day One to day Seven, followed by unopposed estrogen or progestin from day Seven to day Fourteen, depending on the presenting clinical problem.

Prior art has assumed that a specific combination estrogen/progestin oral contraceptive can be formulated in high, intermediate, or low dose levels to satisfy all patients' clinical needs. This assumption, however, fails to consider that individual patients, either those considering oral contraception or menstrual cycle regulation, require specific estrogen or antiestrogen (progestin) replacement in the normal or abnormal menstrual cycle.

It is widely recognized among reproduction endocrinologists that proper folliculogenesis is necessary for subsequent ovulation, and a proper corpus luteum ensures immediate and future menstrual cycle control. Disturbed ovulation or anovulatory disorders account for 75% of clinical functional menstrual disorders and are invariably associated with inappropriate inter-relationships between endogenous estrogen and hypothalamic-pituitary release of FSH (the graafian follicles growth hormone) and LH (the pituitary hormone whose mid-cycle peak is associated with ovum release and the development of a proper functioning corpus luteum).

Prior art administration of high, intermediate, or low dosage combination estrogen/progestin disturbs this follicular phase, FSH-estrogen-LH, inter-relationship by overwhelming sustained suppression of hypothalamic-pituitary LRF, FSH, and LH, thus laying the physiologic possibility for the pre-treatment (normal ovulatory) contraceptive patient to develop future anovulation menstrual cycles after prolonged administration of exogenous sex steroids in the combination pill.

Likewise, this invention provides for flexibility in treating the menstrual dysfunction patient who has endogenous dearrangement in her follicular phase FSH-estrogen-LH interrelationship.

This invention, method and formulation for the delivery of exogenous estrogen and/or progestin, recognizes that contraception and menstrual dysfunction patients present with follicular phases that are euestrogenic, hypoestrogenic, or hyperestrogen. The delivery system of the invention provides a flexibility that allows treatment of the follicular phase, independent of the corpus luteum phase. Likewise, follicular-luteal sex steroid replacement provides for independent corrective management of the luteal phase. Prior art, ignoring these physiologic principles, has been associated with "post pill" ovulation and corpeus luteum disturbance.

Hence, patients using the prior art combination pill for contraception have encountered difficulty in obtaining desired pregnancy after long term administration ("post pill anovulation"). This difficulty, because of the continuous contraphysiologic suppression effect on Hypothalmic-Pituitary maturation centers of the prior art dosages, may persist for an extended time. Further because vasectomy, labroscopy BPS, and other forms of sterilization have become acceptable methods for long term birth control, the prior art combination birth control pill, because of its long term metabolic side effects may be unacceptable, when compared to other feasible non-pharmacological methods. The follicular-luteal method of the present invention, however, because it allows a prompt return of ovulation is ideal for pregnancy spacing and family planning uses in patients who want reliable temporary contraception but who plan future pregnancies and wish to minimize estrogen/progestin metabolic effects in long term users.

The present invention achieves contraception and menstrual cycle regulation by effecting dysrhythmia of FSH and LH, and physiologically provides for postantral follicular development in the proliferative phase of the cycle, and initiates estrogen dependent LRF positive feedback and pituocyte sensitization in the second half of the follicular phase in the hypoestrogen patient.

Likewise, unopposed progestin serving as an anti estrogen at the hypothalmus and pituitary in the second half of the follicular phase enhances endogenous FSH and stimulates late follicular endogenous estrogen production in appropriate amounts and with a proper temporal relationship in euestrogen and hyperestrogen patients.

The distinction between (1), selective FSH, LH suppression and/or temporal stimulation resulting in endogenous FSH and LH dysrhythmia in normal patients;

and, (2), corrective FSH, LH and estradiol 17B modulation in abnormal patients becomes apparent after use of the follicular luteal system when compared to continuous Hypothalmic-Pituitary suppression resulting from the widely used prior art dosages of combination steroids. Thus, the present invention is more suitable than combination methods for the treatment of menstrual dysfunction, as well as for contraception, depending on the patient's clinical classification. No other formulation or steroid administration cycle permits this dual clinical pharmacologic approach.

The follicular phase of the normal or abnormal menstrual cycle may be classified as euestrogenic, hyperestrogenic, or hypoestrogenic. Prior art treats all these clinical situations similarly, while follicular-luteal sex steroid replacement allows constructive pharmacologic alternatives. With the method of the invention, in the second half of the follicular phase, euestrogenic and hyperestrogenic patients, selectively, are administered unopposed low dose progestin to minimize endogenous LH and allow for endogenous FSH. Hypoestrogen patients receive unopposed exogenous low dose estrogen to provide for endogenous LRF and LH, as well as to prime an otherwise inactive endometrium. This flexibility in managing the follicular phase of the menstrual cycle provides a striking distinction with the prior art and its associated continuous sustained suppression of FSH, LH, endogenous estradiol 17B, and the endometrium. However, with the invention there is selective FSH and LH modulation with temporal stimulation of FSH in the first half of the follicular phase and augmentation of LH in the second half of the follicular phase of the treatment cycle, creating a dysrhythmia of FSH and LH, rather than continuous sustained suppression of prior art dosage methods.

Because the follicular-luteal method and pharmaceutical dosage system of the invention depends upon phase, dosage, and temporal relationships of exogenous steroid administration in a cycle which is superimposed over the endogenous cycle of the presenting patients, the invention may be more clearly understood by reference to the drawings.

FIG. 1 depicts the relative blood levels and their interrelationship in a "normal" ovulatory menstrual cycle of FSH, indicated by 1, LH, 2, Estradiol 17B, 3, and progesterone, 4, as measured by radioimmunoassay, charted on an axis of days One through Twenty-eight, the days of one menstrual cycle. The key to the interrelationship of FSH and LH in the normal cycle is endogenous Estradiol 17B and progesterone (an antiestrogen). In the normal cycle, the follicular phase occurs from approximately day One through day Fifteen and culminates prior to ovulation with a peak of endogenous estrogen. The corpus luteum phase occurs from about day Fifteen through day Twenty-eight.

From day One to day Nine there is virtually no Estradiol 17B (100 pg/ml) and progesterone is absent. Prior art steroid dosages of endogenous combination estrogen/progestin wholly ignore this endogenous physiological state as did sequential formulations. The present invention, however, administers no synthetic estrogen or progestin in the early days of the cycle (day One to day Seven) and mimicks this endogenous phenomenon.

In the normal cycle from day Nine to day Fourteen, virtually no endogenous progesterone occurs, however Estradiol 17B rises continually. From day Nine to day Fifteen there is unopposed estrogen elaborated by the ovary. No significant amount of progesterone appears in the second half of the follicular phase of the normal cycle until about twenty-four to thirty-six hours before ovulation. The present invention mimicks this picture in the management of the hypoestrogen patient. In the euestrogen or hyperestrogen patient the invention uses an antiestrogen (synthetic progestin) from day Seven to day Fourteen. This is one of the mechanisms of FSH and temporal endogenous estrogen stimulation achieved by the invention at mid cycle.

In the normal cycle significant amounts of estrogen and progestin concomitantly are found endogneously for approximately seven to ten days out of the menstrual cycle. The normal cycle reveals estrogen (about 300 pg/ml) from day Fourteen to day Twenty-four. Endogenous progesterone is found in excess of 4 ng/ml only from day Eighteen to day Twenty-five. It is most important to note that Estradiol and progesterone concurrently appear in the normal cycle at any dose level for only seven to ten days out of the menstrual cycle. This is an important biological principle ignored by the prior art continuous administration of combination exogenous steroids. As noted earlier, prolonged exposure to estrogen and progestin are associated with minor to catastrophic changes in liver function, i.e., hepatic excretory capabilities, hepatic abnormal synthesis of particular plasma proteins, and hepatic tumors.

Also, characteristic of the normal menstrual cycle is that in the corpus luteum phase of the cycle, both estrogen and progesterone gradually increase from day Fifteen to day Nineteen and gradually subside, terminally, from day Twenty-four to day Twenty-seven. This fact is ignored by prior art, but is applied in this invention's arbitrary corpus luteum which provides a short term (seven to ten days) predictable FSH and LH suppression which also maintains the integrity of the uterine endometrium. This seven to ten day FSH and LH suppression in the invention is preceded by a gradual elevation of estrogen/progestin (four days) and followed by a terminal decrease of both estrogen/progestin as occurs in the normal menstrual cycle.

Figure 2:
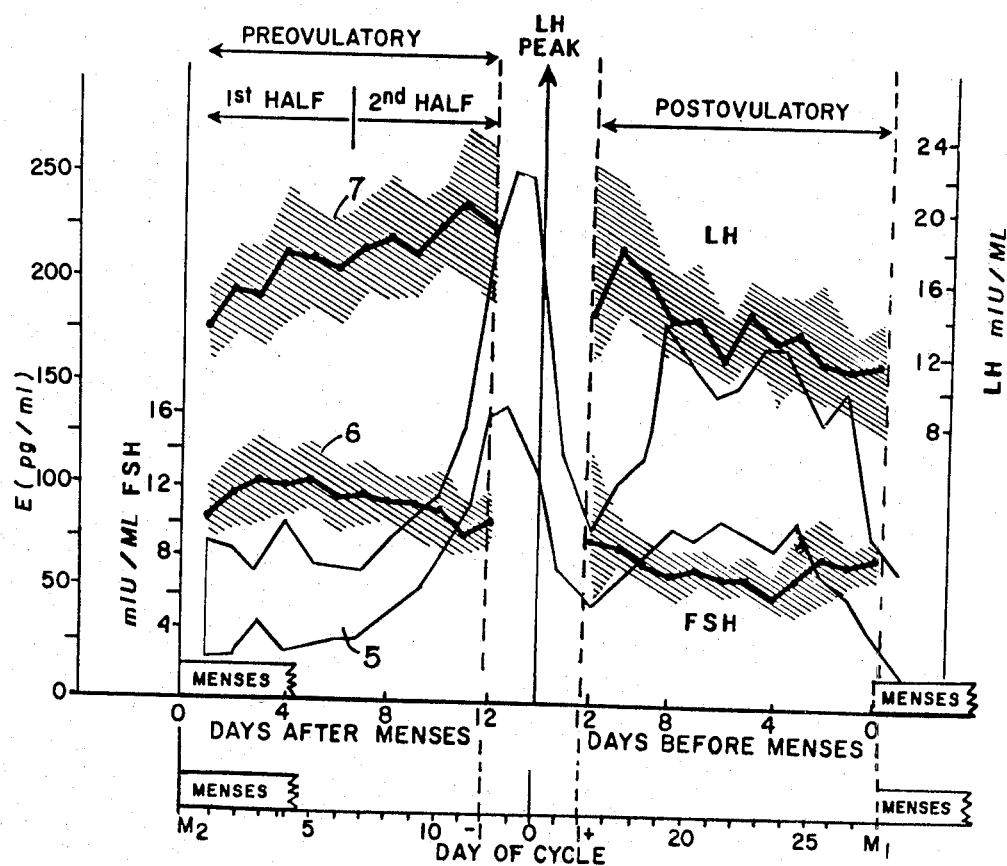
FIG. 2 depicts a normal range of endogenous estrogen FSH and LH serum levels throughout the normal menstrual cycle.

FIG. 2 depicts approximate ranges of endogenous estrogen, 5, FSH, 6, and LH, 7, levels through the days of one normal menstrual cycle. The follicular phase (preovulatory) is divided into a first half (days One-Seven) with no or little estrogen and a second half (days Seven-Thirteen) with ascending levels of endogenous estrogen. Ovulation occurs immediately after the endogenous estrogen peak.

After ovulation, endogenous estrogen falls (days Thirteen-Sixteen); it, however, later, gradually builds up in the early corpus luteum (post ovulatory) phase of the normal menstrual cycle (days Sixteen-Twenty-five). Estrogen production in the terminal portion of the normal corpus luteum phase gradually decreases (days Twenty-five and Twenty-eight), thus allowing for premenstrual partial recovery of endogenous FSH.

Figure 3:
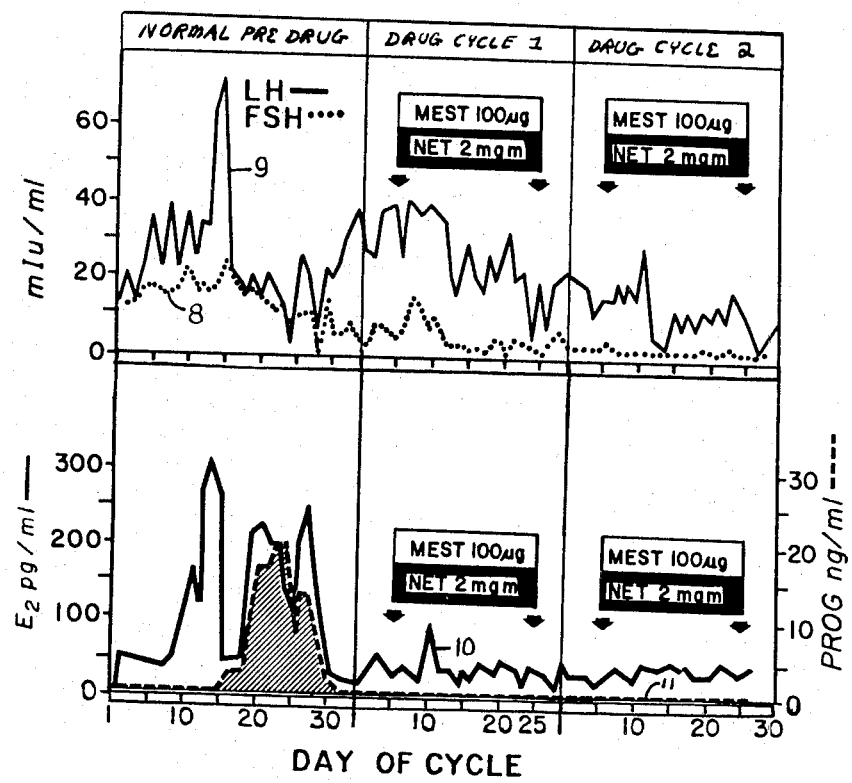
FIG. 3 separately plots daily blood levels of LH and FSH and estrogen and progesterone in a normal ovulatory patient for one cycle and in the same patient through two further cycles during which the patient is administered a prior art combination estrogen/progestin sex steroid contraceptive. The suppressive effect of such prior art administration upon the hormone levels, after successive cycles is apparent.

FIG. 3 depicts effects on the normal menstrual cycle of the prior art combination pill after administrating for several cycles. Three cycles are shown: normal followed by two cycles of administration of mestranol, (MEST), 0.1 mgm, and norethindrone, (NET), 2 mgm., in combination for twenty-one days during the cycle (prior art as formulated in 1957). The mechanism of action of this prior art method is sustained FSH, indicated in the Figure by 8 and LH, 9, suppression, resulting in persistent suppression of ovarian steroidogenesis and virtual elmination of ovarian estrogen 10, and progesterone, 11. This sustained FSH, LH suppression may be associated with post combination pill anovulation and amenorrhea. Also, as noted, continuous administration of combined exogenous synthetic estrogen/progestin has caused associated metabolic complications.

While several new synthetic progestin molecules and estrogen molecules have been developed, progestin and estrogen steroids are still administered in combination. Repeatedly the combination prior art oral contraceptives have been reformulated because of recurring clinical, metabolic and endocrine side effects. However, in doing so the methodology associated with the steroid administration cycle remained the same, persistent reduction of the estrogen content made possible by the availability of a more potent progestin, or a willingness by the drug manufacturer to sacrifice menstrual cycle control to reduce estrogen dosage. In every instance, the continuous administration of combination estrogen and progestin has remained a constant fixture of the prior art, with suppression results, such as depicted in FIG. 3.

Figure 4:
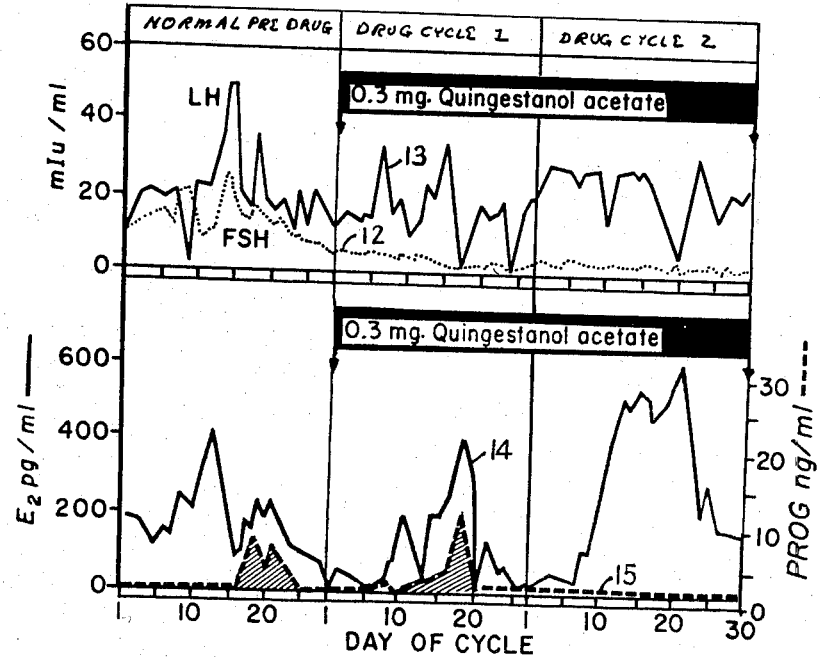
FIG. 4 similarly depicts the endogenous effects of prior art administration of progestin alone upon LH, FSH, estrogen and progesterone through a normal and successive drug cycles.

FIG. 4 depicts effects of the continuous solo administration of the progestin, quingestanol acetate, by oral dosage, for contraceptive use through the normal pre drug cycle and two successive cycles. Neither baseline FSH, indicated by 12, and LH, 13, is suppressed although usually the midcycle peak of LH disappears and ovulation either does not occur or the corpus luteum phase is abnormal. There is unpredictable estrogen production, 14, by the ovary and progesterone is diminished, 15. This accounts for the associated disorderly unpredictable menstrual cycle performance. Intramuscular administration of progesterone, once each three months, has been effective as a contraceptive but is a method plagued with menstrual dysfunction. These progestin alone methods have not been successful, because of the exceedingly low continuation rates resulting from the associated menstrual problems.

Thus, as depicted in FIG. 3, the typical prior art combination pills provide a sufficient dose of estrogen and progestin to prevent ovulation by gross suppression of FSH and LH. This suppression is accomplished by a pharmacological overdose of estrogen and progestin, in combination, daily, for from twenty to twenty-two days during the cycle, followed by a withdrawal period of from six to eight days. The "progestin alone" methods, the "mini-pill" or injectable progestin provide a continuous slow release of progestins. In either the combination pill or "progestin alone" method in the prior art, the exposure of exogenous steroids to the target organs is practically unremitting.

In contrast to these prior art dosages, the follicular-luteal sex steroid replacement of the present invention delivers a drug dosage characterized by temporal relationships of exogenous synthetic estrogen or progestin administered which are analogous to the relationships of endogenous estrogen and/or progesterone in the normal menstrual cycle. Further, unlike the prior art, the present invention recognizes the independent functions and physiologic necessity of preserving the follicular and the corpus luteum stages of the "normal" menstrual cycle to insure future ovulatory menstrual performance and target organ rest from either endogenous or exogenous sex steroids.

In accordance with the present invention, an arbitrary follicular phase and an arbitrary luteal phase of a steroid administration cycle is "superimposed" over a patient's menstrual cycle. In the method of the invention, the steroid administration lasts for approximately twenty-one days, based upon an arbitrary follicular phase which extends for about fourteen days and a following luteal phase of about fourteen days, with a cycle of about twenty eight days, approximating the normal menstrual cycle.

According to the method of the present invention, an administration cycle, approximating a normal menstrual cycle is selected depending on the endogenous estrogen control state of the patient. In the administration cycle, an arbitrary follicular and an arbitrary luteal phase segment, dividing the cycle are determined. In the early stage of the follicular phase, for about seven days, no exogenous steroids are administered. This allows FSH to occur during the beginning part of the cycle so that ovarian folliculogenesis will not be completely suppressed. By reference to FIG. 1, it can be seen that the normal menstrual cycle is thereby mimicked in that estrogen and progesterone do not appear normally in any quantity during this corresponding time. For about the next seven days, a pharmacologically low dose of an unopposed estrogen or progestin steroid is administered daily. Whether the steroid is estrogen or progestin depends upon the specific clinical estrogen state of the patient, i.e., type I hypoestrogen cycle or type II euestrogen or hyperestrogen cycle. This classification determines the completion of the arbitrary follicular stage of the administration cycle in which the early portion of the follicular phase is standardized, while the later portion (day Seven to day Fourteen) is predicated on clinical objectives and the control estrogen status of the patient.

Throughout the following arbitrary luteal stage which is about fourteen days long, combination estrogen and progestin is administered in differing pharmacological doses during various phases of the luteal stage. Early in the arbitrary luteal stage, a pharmacologically low dose of combination estrogen/progestin is administered. The dose of exogenous synthetic estrogen and progestin, and the length of time (number of days and dosage) it is administered, is critical for optimum menstrual cycle function. During the mid stages of the luteal phase, a daily dosage of combination estrogen/progestin, adequate for FSH and LH suppression and endometrium maintenance is administered. At the terminal stage, the dosage of combination estrogen/progestin may be reduced by approximately one-half ($\frac{1}{2}$) but not for more than about three days. Thus the arbitrary corpus luteum is adjusted depending on clinical objectives for the presenting patient, just as the second half of the follicular phase adjusts to the endogenous sex hormone melieu presenting clinically.

In the follicular-luteal method of the present invention, accumulative estrogen dosage as well as the daily dose and total days of administration in a drug cycle is substantially reduced by producing a FSH-LH dysrhythmia in the cycle, rather than by continuous suppression. The contraceptive and menstrual cycle regulating effects of the follicular-luteal sex steroid replacement are independent of the potency of the particular progestins administered, provided that pharmacologically equivalent doses are substituted. The invention provides for predictable endogenous estrogen rather than the total suppression characteristic of current combination pills. The follicular-luteal system avoids long-term unremitting stimulation of target cells with combined estrogen and progestin by administering combined estrogen and progestin in any substantial dose for only about six to ten days out of the cycle. Further, estrogen is administered for only fourteen days out of the cycle in euestrogen and hyperestrogen patients as compared to twenty-one days in prior art low dose combination estrogen/progestin pills. In a dose of any consequence, unopposed estrogen is administered for only six to seven days in the drug cycle for the hypoestrogen patient just as in the normal menstrual cycle.

The follicular-luteal system permits target cells a resting period from exogenous estrogen uptake for a substantial longer period (approximately fourteen days) in the euestrogen and hyperestrogen cycle, as compared to the nominal seven day rest period provided by prior art estrogen/progestin combination pills. Finally, estrogen is only given in combination with progestin, which is known to increase the intracellular concentration of exogenous estrogen, for only about seven to ten days in any significant dose in all clinical situations.

The follicular-luteal system, therefore, minimizes adverse metabolic consequences of both uninterrupted estrogen and large dose exogenous estrogen administered concurrently with progestin. Target cell uptake of exogenous estrogen, the primary cause of endocrine and metabolic adverse side effects, is thereby reduced.

Because estrogen is administered for only about fourteen to sixteen days during the drug cycle and is administered in combination with progestin in any dose of consequence for only six to seven days out of the cycle in the follicular-luteal system the present invention minimizes the opportunity for liver tumors, (adenomas, or nodular hyperplasia) which have been reported on prior art high dose estrogen/progestins. Under the circumstances, uptake of exogenous estrogen by the liver cells appears to be minimized and opportunities for hypertrophy, hyperplasia, or adenomatous phenomena are thereby decreased. Further, the folliculogenicluteotrophic system minimizes combination estrogen/progestin exposure to all target cells, pituitary as well as liver, and minimizes the exposure of these cells to continuous exogenous estrogen during the cycle month while providing effective cycle and fertility control. Consequently, pituitary side effects such as hyperprolactanemia, which may be associated with microadenoma of the pituitary gland, should also be reduced. Such microadenoma, it has been speculated, are produced by a biological mechanism, similar to that which produces liver side effects, i.e., uninterrupted or continuous exposure to combination estrogen/progestin.

As heretofore related, the invention may be adapted in a dosage system for any pharmacologic estrogen and progestin molecule because of the manner in which the invention achieves its effects in distinction to prior art administration systems. Hence, in accordance with the invention, the following currently FDA approved estrogen steroids may be used:

Mestranol [C$_{21}$H$_{26}$O$_2$]. 3-Methoxy-19-nor-17a-pregna-1,3,5 (10)-trien-20-yn-17-ol.

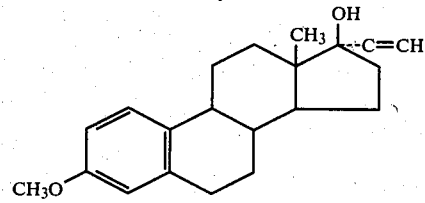

Ethinyl estradiol [C$_{20}$H$_{24}$O$_2$]. 19-Nor-17a-pregna-1,3,5 (10)-trien-

-continued
20-yne-3, 17-diol.

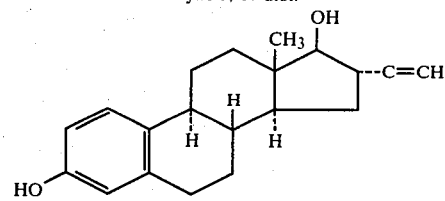

And the following currently FDA approved progestin steroids may be used:

Norethindrone [C$_{20}$H$_{26}$O$_2$]. 17-Hydroxy-19-nor-17a-pregn-4-en-20-yn-3-one.

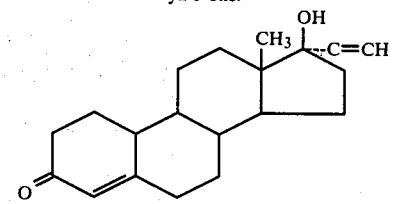

Norethindrone acetate [C$_{20}$H$_{28}$O$_3$]. 17-oxyacetate-19-nor-17a-pregn-4-en-20-yn-3-one.

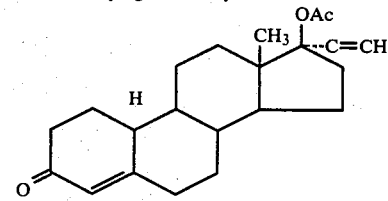

Norethynodrel [C$_{20}$H$_{26}$O$_2$]. 17-Hydroxy-19-nor-17a-pregn-5(10)-en-20-yn-3-one.

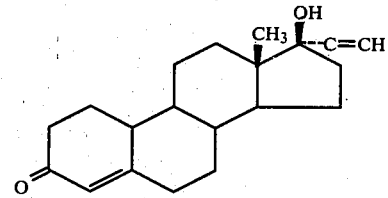

Ethynodiol diacetate [C$_{24}$H$_{32}$O$_4$]. 19-Nor-17a-pregn-4-en-20-yne-3B-17-diacetate.

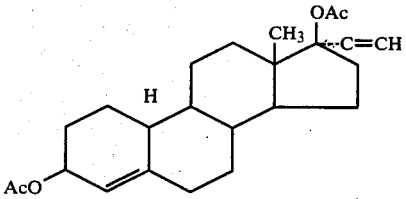

Norgestrel [C$_{21}$H$_{28}$O$_2$]. 13-Ethyl-17-hydroxy-18,19-dinor-17a-pregn-4-en-20-yn-3-one.

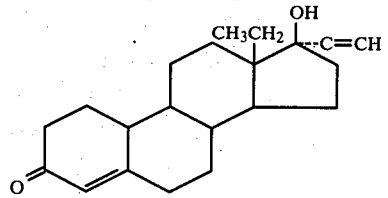

The ontogeny of the invention may be more fully understood in the following Examples of different formulations of steriod delivery systems in accordance with the follicular-luteal Replacement or Supplementation method of the invention.

The examples of the invention resulted from work conducted pursuant to Investigational New Drug Application No. 676 issued by the U.S. Food and Drug Administration.

Figure 5:
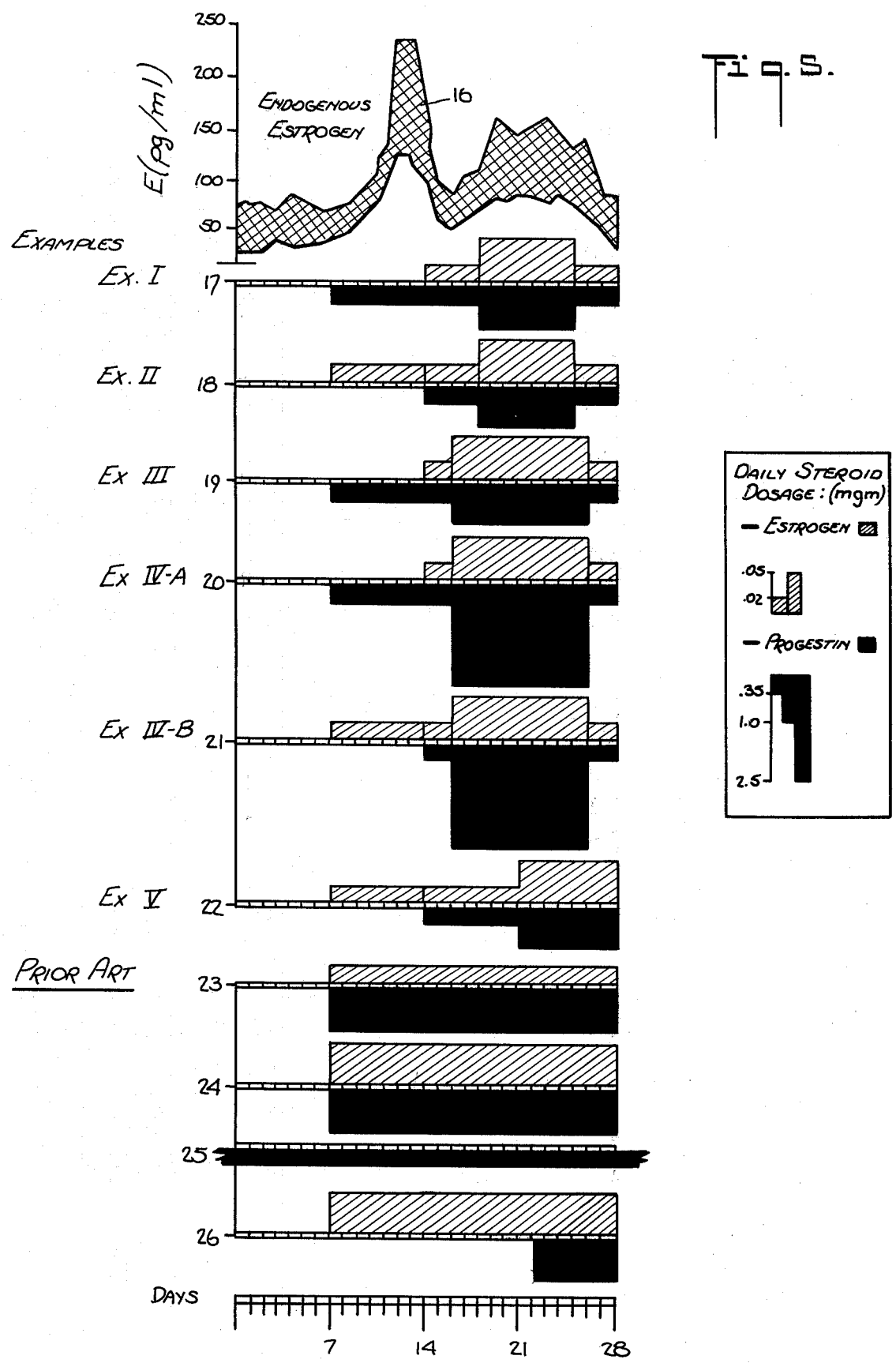
FIG. 5 depicts formulations of examples of the present invention both in daily dose and in distribution of the exogenous synthetic estrogen and progestin administered throughout the menstrual cycle. The distribution of the administered synthetic (exogenous) estrogen is compared to the normal serum (endogenous) estrogen distribution found in a normal ovulatory menstrual cycle, heretofore depicted in FIG. 2.

For clarity in the explanation of the invention, FIG. 5 depicts various follicular luteal formulations set forth as examples herein in qualitative comparison with the range of "normal" endogenous estrogen depicted in FIG. 2 and in quantitative comparison with steroid dosages of prior art combination, progestin "alone," and estrogen sequential formulations through one twenty eight day menstrual cycle/dosage cycle.

In FIG. 5, the qualitive distribution of the range of endogenous estrogen occurring through a normal menstrual cycle is depicted by the crosshatched graph from days One to Twenty-eight, indicated by 16. The daily estrogen/progestin dosage formulations of various examples of the invention for one administration cycle are indicated at 17 depicting Example I; 18 depicting Example II; 19 depicting Example III; 20 depicting Example IV-A; 21 depicting Example IV-B; and 22 depicting Example V.

In comparison with the occurrence of endogenous estrogen and the formulations of the invention, FIG. 5 also depicts estrogen/progestin administration of representative prior art combination pill daily dosages at 23, depicting "Loestrin 1/20" (0.02 mgm. ethinyl estradiol and 1.0 mgm. norethindrone acetate for twenty one days) and at 24, depicting Lo/Ovral.

At 25, FIG. 5 depicts the daily dosage of a "mini pill" progestin alone formulation providing a daily dosage of 0.35 mgm. norethindrone, "Nor-Q.D." At 26, the now discontinued estrogen sequential formulation is depicted.

EXAMPLE I

FIG. 5, at 17, details a follicular-luteal formulation utilizing current prescription available dosages of synthetic estrogen and progestin. This formulation is for management of the euestrogenic and hyperestrogen (non androgenic) patient. Usually, this patient will be, prior to drug, normally ovulating. This formulation which is designed for a 28 day treatment cycle, beginning with the onset of menstruation, follows:

low dose progestin. The corpus luteum phase has ascending low dose combination estrogen/progestin for four days; adequate combination estrogen/progestin for FSH, LH suppression and endometrial integrity for seven days; and terminal low dose estrogen/progestin for three days. The regimen embodies only fourteen days of exogenous estrogen, fourteen days of recovery from exogenous estrogen, and only seven days of substantial amounts of estrogen/progestin. The follicular phase progestin (day Seven to Fourteen) allows for endogenous FSH. The early corpus luteum combination estrogen/progestin provides for moderate ovarian synthesis of endogenous estrogen (which is a factor in breakthrough bleeding.) Terminal low dose estrogen/progestin minimizes the dose of exogenous estrogen/progestin and provides for predictable withdraw bleeding and recovery of pituitary FSH and LH. This Follicular Progestin Luteal Replacement (FPLR) formulation provides for the lowest amount of exogenous estrogen, with the longest possible recovery period by the target organs from exogenous estrogen, with minimal amounts of combination estrogen/progestin, and attains 75% good menstrual cycle control. It represents the minimum amount of low dose combination feasible in the early and terminal portion of the corpus luteum. The continuation rate looks to be 65% compared to 50 to 60% in the prior art of combination estrogen/progestin, 35% in most low dose combination, and 25% in progestin alone. The clinical complication of consequence is breakthrough bleeding and menstrual cycle control. In this formulation, late follicular phase unopposed progestin and early arbitrary corpus luteum low dose combination (4 days) allows midcycle endogenous estrogen in the range of 250–450 pg/ml thus having a salutary modulating effect on the hypothalamic-pituitary-ovarian axis. The formulation of this Example however, is not optimum for all clinical situations, i.e., patients with hypoestrogen (vasomotor symptomatic climacteric, primary amenorrhea, secondary amenorrhea with failure of progestin withdrawal hypoestrogen oligomenorrhea). For these clinical situations, Example II is the alternate preferred formulation.

| Follicular Progestin Luteal Replacement (FPLR) | | | |
|---|---|---|---|
| Segment Days | Day | | Daily Dosage |
| | Follicular stage | | |
| 7 | 1 through 7 (early) | | No exogenous steriods. |
| 7 | 8 through 14 (late) | (progestin) | .35 mgm. Norethindrone |
| | Luteal stage | | |
| 4 | 15 through 18 (early) (low dose combination) | (progestin) and | .35 mgm. Norethindrone |
| | | (estrogen) | .02 mgm. Ethinyl Estradiol. |
| 7 | 19 through 25 (mid) (regulation dose combination) | (progestin) and | 1.0 mgm. Norethindrone Acetate. |
| | | (estrogen) | .05 mgm. Ethinyl Estradiol. |
| 3 | 26 through 28 (late) (reduced dose combination) | (progestin) and | .35 mgm. Norethindrone |
| | | (estrogen) | .02 mgm. Ethinyl Estradoil. |

Total Cycle Dosage:
11.9 mgm. Norethindrone and Norethindrone Acetate
.49 mgm. Ethinyl Estradiol This example embodies a discreet follicular phase of fourteen days and a corpus luteum phase of fourteen days. The follicular phase second half has unopposed

EXAMPLE II

Under Example I of follicular-luteal system, reasonable predictable periods may be expected; however, in primary amenorrhea, and secondary amenorrhea due to endogenous hypoestrogenism the follicular-luteal system may be associated with scanty periods or ultimate secondary amenorrhea because of the lack of Follicular phase estrogen priming of the endometrium and the second half of the Follicular phase progestin only folowed by simultaneous estrogen/progestin administered in the first part of the corpeus luteum followed by 7 days of larger dose estrogen/progestin and subsequent terminal low dose estrogen/progestin withdrawal. Under these circumstances, dosage of Ethinyl Estradiol, 0.02 mgm., is substituted for the dosage of Norethindrone, 0.35 mgm., in the second half of the follicular phase of the steroid cycle. This allows adequate estrogen priming, to the hypothalmus, pituitary, as well as the endometrium, prior to the exposure of corpus luteum simultaneous estrogen/progestin. Secondary amenorrhea and breakthrough bleeding is thus minimized and estrogen stimulation of the LRF-LH feedback system is initiated.

By this alteration of the follicular-luteal system, several physiologic functions are accomplished. In the second half of the follicular phase of the cycle, priming of the endometrium occurs prior to exposure to the corpus luteum dose of estrogen/progestin. Simultaneously, FSH is blunted, at most minimally suppressed and not for a prolonged sustained period of time, LRF is activated and the pituocyte sensitized by unopposed estrogen for LH synthesis and storage.

Because secondary amenorrhea due to exogenous estrogen/progestin on a long-term basis is clinically undesirable, it is possible to use a primary follicular-luteal system such as Example I to perform one physiologic function and a modified follicular-luteal system, such as Example II in which estrogen is substituted for the follicular phase mini-dose of progestin, to perform a different physiologic function. The systems would alternate depending on clinical and physiologic requirements. In this regimen, FSH activity occurs in the follicular phase of Example I whereas with Example II, minimal suppression of endogenous FSH may occur; meanwhile, there is activation of the LRF-LH estrogen dependent system. With Example I less priming of the endometrium occurs in hypoestrogen patents since the corpus luteum is preceeded with progestin only, whereas Example II allows judicious priming of the endometrium since the corpus luteum is preceeded with exogenous estrogen the second half of the follicular phase. Thus, better estrogen endometrial priming is allowed, but long-term sustained suppression of FSH or LH or both is prevented.

This modification of the formulation of Example I is best suited to patients in a hypoestrogen clinical state where LRF exosure to unopposed estrogen is lacking and breakthrough bleeding and secondary amenorrhea are a problem. This formulation is identical to Example I, except that exogenous estrogen is substituted for progestin to provide for endometrial priming and LRF and LH stimulation from day Seven to day Fourteen of the drug administration cycle. FIG. 5 depicts this formulation for one administration cycle at 18.

| Follicular Estrogen Luteal Replacement (FELR) | | |
|---|---|---|
| Segment Days | Day | Daily Dosage |
| Follicular stage | | |
| 7 | 1 through 7 | No exogenous steriods. |
| 7 | 8 through 14 | .02 mgm. Ethinyl Estradiol |
| Luteal stage | | |
| 4 | 15 through 18 | .35 mgm. Norethindrone<br>.02 mgm. Ethinyl Estradiol |
| 7 | 19 through 25 | 1.0 mgm. Norethindrone Acetate<br>.05 mgm. Ethinyl Estradiol |
| 3 | 26 through 28 | .35 mgm. Norethindrone<br>.02 mgm. Ethinyl Estradiol |

Total Cycle Dosage:
9.45 mgm. Norethindrone and Norethindrone Acetate
.63 mgm. Ethinyl Estadiol In the present art, for the hypoestrogen presenting state, a physician would prescribe two different pills to meet this clinical situation and hope the patient understands complex instructions. (Which pill when?) Further, the hypoestrogen situation requires follicular phase unopposed estrogen to prime the endometrium and stimulate estrogen dependent LRF and LH. In contradistinction to the therapeutic regimine of Example II, all prior art combination estrogen/progestin steroid dosage systems accomplish the opposite and produce atrophic endometrium and suppress LRF, FSH, and LH. By comparison of the incidence of endogenous estrogen, 16, in FIG. 5, with this Example, at 18, it is apparent how the invention's alternate follicular-luteal formulation solves this clinical dilema by priming the endometrium and initiating endogenous estrogen dependent LRF and LH due to unopposed follicular phase estrogen. Yet it is quite different than an earlier alternative to combination estrogen/progestin, i.e. sequential administration, depicted in FIG. 5 at 26, when unopposed large dose (FSH suppressive) ethinyl estradiol or its 3-methyl analog were administered for sixteen days unopposed and for five days opposed by progestin. Here the problem of associated endometrial carcenoma was reported as was escape ovulation. More importantly early arbitrary corpus luteum low dose combination administered through day Fifteen through day Eighteen of Example II stimulates endogenous estrogen to a level 150–250 pg/ml, thus initiating activity in the hypothalamic-pituitary-ovarian axis. This occurs without resorting to the juggling of different pills on different days which is now standard practice for this clinical situation. The other current erroneous alternative prescribed is the use of combination estrogen/progestin, because combination steroids are convenient; however, this is contraphysiologic and therefore inappropriate therapy.

The formulation of this Example is useful also for treating breakthrough bleeding occurring during the administration of Example I if progestin from day Seven to day Fourteen does not adequately prime the pre-arbitrary corpus luteum endometrium.

EXAMPLE III

Other clinical complications such as breakthrough bleeding require therapeutic flexibility not possible with prior art combination estrogen/progestin for which the follicular-luteal system has been slightly altered. Some oligomenorrhea, secondary amenorrhea patients do not have hypoestrogenism but have hyperestrogenism. Hyperestrogen patients may have polymenorrhea, menorrhagia, hypermenorrhea or menometrorrhagia. Such patients are anovulatory. For those clinical states prior art combination estrogen/progestin steroid administration is currently used, and is satisfactory only for stopping menstrual flow but it aids and abets an already deranged hypothalamic-pituitary axis and certainly does not institute a physiological corrective hormone milieu.

Irregular bleeding patients should be stopped promptly and predictably by using an arbitrary corpus luteum FSH, LH suppressive dose and endometrial maintenance dose three times daily for seven days, i.e., Norethindrone acetate 1.0 mgm and ethinyl estradiol 0.05 mgm. Bleeding will stop and a withdrawal period will ensue within one week. This class of patient, hyperestrogenic oligomenorrhea, secondary amenorrhea or menstrual irregular anovulatory patient, after adequate FSH, LH and ovarian short term suppression and endometrial medical curretage should be cycled with a follicular-luteal system as follows to ensure cycle control and inhibit breakthrough bleeding for a short period of about three to six months. This steroid cycle of the invention is depicted at 19 in FIG. 5.

| Segment Days | Day | Daily Dosage | |
|---|---|---|---|
| | | Follicular stage | |
| 7 | 1 through 7 (early) | No exogenous steriods. | |
| 7 | 8 through 14 (late) | .02 mgm. | Ethinyl Estradiol. |
| | | Luteal stage | |
| 2 | 15 through 16 (early) | .35 mgm. | Norethindrone |
| | | .02 mgm. | Ethinyl Estradiol. |
| 10 | 17 through 26 (mid) | 1.0 mgm. | Norethindrone Acetate |
| | | .05 mgm. | Ethinyl Estradiol |
| | | Luteal stage | |
| 2 | 27 through 28 (late) | .35 mgm. | Norethindrone |
| | | .02 mgm. | Ethinyl Estradiol. |

Thereafter the patient should be reduced to the more physiologic low dose follicular-luteal formulation of FELR, Example I or FPLR, Example II.

EXAMPLE IV

Breakthrough bleeding is a major deterrent to the satisfactory continuation rate with prior art attempts to reduce estrogen dosages of prior art combination oral steroid contraception regimens. This is especially true of the low dose combination estrogen/progestins with the exception of Lo/Ovral. Prior art options for clinical management of breakthrough bleeding, i.e., double the dose of the estrogen/progestin on which breakthrough occurred, change to a biologic more potent pill, e.g., (estrogen dominant "Enovid", progestin-androgen dominant "Ovral"), dilation and curettage, or hysterectomy, are all undesirable alternatives.

When prior art combination dosages are employed, the pathophysiology of spontaneous irregular bleeding or breakthrough bleeding involves inappropriate priming of the endometrium and pharmacologic overdose of simultaneous exogenous estrogen and progestin. Maturation and subsequent unpredictable dissolution of the endometrium occurs. Combination estrogen/progestin overstimulates and disrupts interrelationships of the endometrial components, glands, stroma, and vasculature, ultimately initiating an exhausted atrophic state. Although hypomenorrhea may ensue, many times breakthrough bleeding or amenorrhea occurs. Therapeutic steroid dosages of the prior art fail to make reasonable provisions for transient or long-term management of oral contraceptive induced hypomenorrhea (which many consider salutory), meno-metrorrhagia, breakthrough bleeding, or secondary amenorrhea. The follicular-luteal replacement steroid dosage system of the present invention can be adopted to treat these untoward bleeding patterns.

Hence, the following follicular luteal formulations, as well as Example II or III, were administered:

EXAMPLE IV-A

| Segment Days | Day | Daily Dosage | |
|---|---|---|---|
| | | Follicular Stage | |
| 7 | 1 through 7 (early) | No exogenous steroids | |
| 7 | 8 through 14 (late) | .35 mgm. | Norethindrone |
| | | Luteal Stage | |
| 2 | 15 through 16 (early) (low dose combination) | .35 mgm. | Norethindrone |
| | | .02 mgm. | Ethinyl Estradiol |
| 10 | 17 through 26 (mid) (regulation dose combination) | 2.5 mgm. | Norethindrone acetate |
| | | .05 mgm. | Ethinyl Estradiol |
| 2 | 27 through 28 (late) (reduced dose combination) | .35 mgm. | Norethindrone |
| | | .02 mgm. | Ethinyl Estradiol |

Total Cycle Dosage:
28.85 mgm. Norethindrone and Norethindrone Acetate
.58 mgm. Ethinyl Estradiol This formulation, depicted at 20 in FIG. 5, is an appropriate treatment if breakthrough bleeding occurs with the formulation of Example I and for spontaneous menorrhagia, hypermenorrhea, or menometorrhagia in the euestrogen or hyperestrogen state.

Here, day Seven through day Fourteen of the follicular phase has low dose progestin to counteract endogenous estrogen. Early corpus luteum combination estrogen/progestin is reduced to two days to minimize synthesis of ovarian endogenous estrogen, a factor in breakthrough bleeding. Terminal reduction to two days of corpus luteum low dose combined estrogen/progestin minimizes premature withdrawal bleeding. The ten days of combination estrogen/progestin mid corpus luteum include progestin and exogenous estrogen at a dose to suppress FSH, LH and to mature and maintain the endometrium.

EXAMPLE IV-B

| Segment Days | Day | Daily Dosage | |
|---|---|---|---|
| | | Follicular Stage | |
| 7 | 1 through 7 (early) | No exogenous steroids | |
| 7 | 8 through 14 (late) | .02 mgm. | Ethinyl Estradiol |
| | | Luteal Stage | |
| 2 | 15 through 16 (early) (low dose combination) | .35 mgm. | Norethindrone |
| | | .02 mgm. | Ethinyl Estra- |

| Segment Days | Day | Daily Dosage | |
|---|---|---|---|
| | | | diol |
| 10 | 17 through 26 (mid) (dose combination) | 2.5 mgm. | Norethindrone Acetate |
| | | .05 mgm. | Ethinyl Estradiol |
| 2 | 27 through 28 (late) (reduced dose combination) | .35 mgm. | Norethindrone |
| | | .02 mgm. | Ethinyl Estradiol |

Total Cycle Dosage:
26.4 mgm. Norethindrone and Norethindrone Acetate
.72 mgm. Ethinyl Estradiol This follicular-luteal sex steroid replacement formulation depicted at 21 in FIG. 5 is administered for the management of menstrual dysfunction, hypermenorrhea, menorrhagia, menometrorrhagia, breakthrough bleeding, on a short term basis for approximately three to six months and is identical to Example III, except in the mid corpus luteum combination estrogen/progestin, progestin is doubled in dose to minimize breakthrough bleeding. This formulation is the highest dose replacement regimen designed to provide follicular phase unopposed estrogen, endometrial priming, and a substantial estrogen/progestin replacement in the corpus luteum phase to maximize mentrual cycle control.

In Examples IV-A and IV-B, early corpus luteum low dose combination estrogen/progestin has been shortened to two days to minimize the ovarian synthesis and release of endogenous estrogen whose withdrawal is coincident with arbitrary corpus luteum breakthrough bleeding. Further, these examples have increased doses of estrogen/progestin in the arbitrary corpus luteum (day Seventeen to day Twenty-six) to more adequately maintain the endometrium in the second half of the menstrual cycle. With these adaptations, the follicular-luteal replacement system allows for transient treatment for about three to six months of breakthrough bleeding without changing the drug or resorting to prolonged excessive and needless estrogen/progestin target cell exposure i.e. doubling the dose. Thus follicular-luteal replacement with minor changes in dose and temporal relationship has provided for a continuing clinical treatment if breakthrough bleeding and secondary amenorrhea are encountered.

EXAMPLE V

For clinical states associated with hypoestrogenism, specifically, secondary amenorrhea, follicular phase estrogen replacement is appropriate. The following formulation provides endogenous estrogen in the late follicular and low dose estrogen/progestin in the first half of the luteal phase of the cycle, but has been associated with luteal phase breakthrough bleeding. In FIG. 5, this formulation is depicted at 22.

EXAMPLE V

| Segment Day | Day | Daily Dosage | |
|---|---|---|---|
| | Follicular Stage | | |
| 7 | 1 through 7 (early) | No exogenous steroids | |
| 7 | 8 through 14 (late) | .02 mgm. | Ethinyl Estradiol |
| | Luteal Stage | | |
| 7 | 15 through 21 (early) | .35 mgm. | Norethindrone |

| Segment Day | Day | Daily Dosage | |
|---|---|---|---|
| | (low dose combination) | .02 mgm. | Ethinyl Estradiol |
| 7 | 22 through 28 (late) (dose combination) | 1.0 mgm. | Norethindrone Acetate |
| | | .05 mgm. | Ethinyl Estradiol |

Total Cycle Dosage:
9.45 mgm. Norethindrone and Norethindrone Acetate
.63 mgm. Ethinyl Estradiol This follicular-luteal formulation is designed for the management of the hypoestrogenic or 2° amenorrheic patient. Note the endogenous FSH, LH, and estrogen throughout the cycle during its administration. There is an initial seven day recovery period post pill cycle. Days Seven to Fourteen administer unopposed exogenous estrogen to stimulate LRF and/or LH activity. Seven days of low dose estrogen/progestin, from day Fourteen to day Twenty-one, after unopposed exogenous estrogen allows elaboration of endogenous estrogen. This is important in the positive feedback mechanism to the hypothalamus and pituitary as well as to further prime the endometrium. The final seven days of a FSH, LH suppression dose of combination estrogen/progestin matures the endometrium and provides for a predictable withdrawal period.

Breakthrough bleeding may be a factor if there is endogenous estrogen elaboration and its subsequent withdrawal in the luteal part of the cycle. This formulation, however, like that in Example II is designed to provide for hypothalamic, pituitary, and ovarian reactivation and breakthrough bleeding is an acceptable side effect in these patients.

EXAMPLE VI

Figure 6:
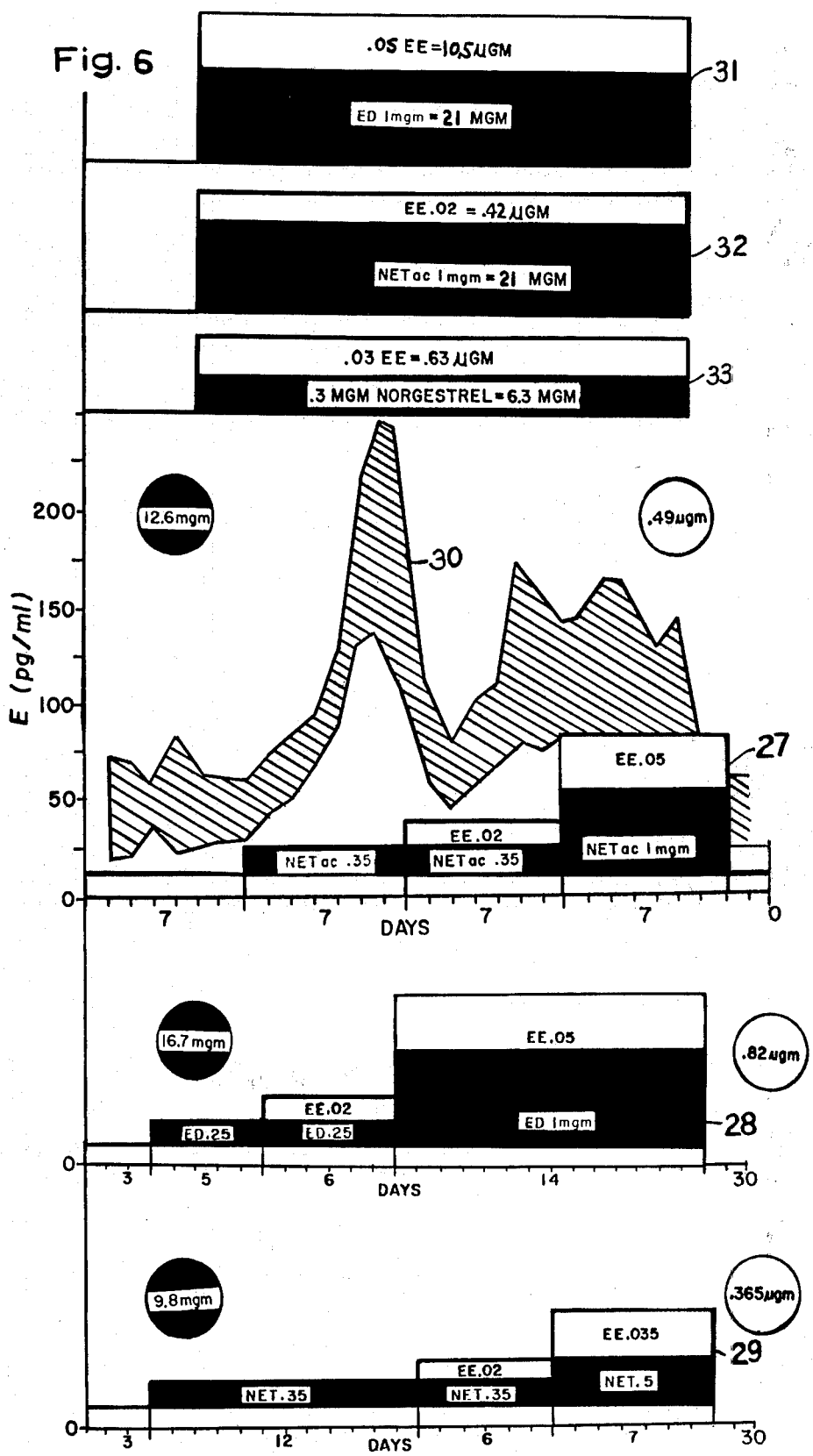
FIG. 6 depicts various other examples of follicular-luteal formulations of the present invention, also in comparison, in terms of daily dosage, distribution of exogenous steroids through the cycle, and total drug administration in one cycle, with prior art combination formulations using the same steroid components of the examples, against a background of endogenous estrogen distribution.

This formulation is depicted in FIG. 6 at 27. In FIG. 6 the administration of a daily exogenous dose of progestin and estrogen/progestin throughout one cycle is represented with other examples of the invention at 28 and 29 in comparison with the range of endogenous estrogen, 30, and with daily and total cycle dosages of combination formulations using similar steroids at 31, 32 and 33. This formulation was initiated to be used with Norethindrone as well as Norethindrone Acetate and is also useful with Ethinyldiol Diacetate and Norgestrel.

Here, as depicted in FIG. 6 at 27, an arbitrary follicular phase and an arbitrary luteal phase occur in a twenty-eight day cycle, not too different in time frame from the follicular and corpus luteum stages of the normal menstrual cycle.

Dosage, beginning with the first day of a menstrual period, was as follows during the days of the cycle:

| Segment Days | Day | Daily Dosage | |
|---|---|---|---|
| | Follicular stage | | |
| 7 | 1 through 7 | No exogenous steriods. | |
| 7 | 8 through 14 | .35 mgm. | Norethindrone |
| | Luteal stage | | |
| 7 | 15 through 21 | .35 mgm. | Norethindrone and |
| | | .02 mgm. | Ethinyl Estradiol. |
| 7 | 22 through 28 | 1.0 mgm. | Norethindrone Acetate. and |

| Segment | | |
|---|---|---|
| Days | Day | Daily Dosage |
| | | .05 mgm. Ethinyl Estradiol. |

Total Cycle Dosage:
11.9 mgm. Norethindrone and Norethindrone Acetate
.49 mgm. Ethinyl Estradiol In this Example, as in Example I, in the follicular phase of the drug cycle, day One through day Fourteen, dysrhythmia of the relationship between FSH and LH prevented breakthrough or impromptu ovulation. The seven day initial period of no drug lengthened the amount of time endogenous estrogen and progesterone were absent during the first half of the follicular phase of the patient's menstrual cycle. This provided a recovery period for the hypothalmus and pituitary for FSH and LH. Likewise it provides a period of rest for the liver from exogenous estrogen and progesten exposure.

By administering a small dose of progestin in the second half of the follicular phase for only seven days, FSH stimulation in the late follicular phase was intiated. Thus, by combining no drug for seven days followed by low dose progestin for the next seven days, a follicular phase of roughly fourteen days is provided in which both endogenous FSH and LH activity occur. Throughout the late follicular and early luteal phase of the treatment cycle endogenous estrogen is not suppressed. This is in contrast to the gross suppression of FSH, LH and endogenous estrogen depicted in FIG. 3 in which hormone levels of a comparable patient administered a combination pill are depicted.

Thus, a rest period of from fourteen to sixteen days from exogenous estrogen was provided. Low dose estrogen/progestin is administered for only seven days in the first half of the corpus luteum phase of the cycle. Significant breakthrough bleeding did not occur. A sufficient amount of estrogen/progestin, not to exceed seven to ten days, is administered in the second half of the corpus luteum to effect predictable FSH and LH suppression, which is analogous to the suppression occurring during the comparable time period in a normal menstrual cycle. A recovery period from exogenous estrogen of fourteen days in the follicular phase of the cycle of Example VI and a recovery period from significant amounts of exogenous sythetic progestin was maintained for twenty-one days, throughout the drug cycle of this example. Extensive hypothalamic and pituitary suppression were thus prevented.

By minimizing both the dose and length of time of administration of exogenous estrogen, end organ recovery from continuous exogenous estrogen administration is allowed.

The dosage of this Example may be compared with the dosage of Lo/Ovral, 33, in FIG. 6 and Loestrin 1/20, 32. Contrast of the rhythmic administration of the Example, which provides planned dose levels, temporal relationships, and ratios of exogenous estrogen and progestin analogous with identifiable stages of the occurrence of endogenous estrogen and progesterone in the normal cycle, with the unremittingly uniform dose of exogenous steriods throughout the cycle provided by the combination pill is apparent. The uniform dosage of estrogen and progestin throughout the cycle by the combination pill is without regard to the occurrence of endogenous estrogen in the cycle or the recovery of endogenous estrogen post treatment cycle. In contrast, the follicular-luteal dosage of this Example provides distinct follicular and luteal phases of exogenous and/or endogenous estrogen dosage, analogous to the occurrence of endogenous estrogen in the normal cycle and more importantly allows for a predictable surge of endogenous estrogen in the late follicular early luteal phase of the cycle.

EXAMPLE VII

Total cycle dosages of selected Examples are representatively compared with Lo/Ovral, a combination pill having the best current performance characteristics, and other combination pills using similar steroid components as the Examples:

| Formulation | Daily Dosage | Total Cycle Dosage | Reduction Achieved by Ex. 1 and Ex. VI | |
|---|---|---|---|---|
| | | | Estrogen | Progestin |
| Example I | — | 11.9 mgm. NET .49 mgm. EE | | |
| Example VI | — | 11.9 mgm. NET .49 mgm. EE | | |
| Lo Ovral | .3 mgm. NORG .03 mgm. EE | 6.3 mgm. NORG .63 mgm. EE | 22% | — |
| Loestrin 1/20 | 1.0 mgm. NET .02 mgm. EE | 21 mgm. NET .42 mgm. EE | −16% | 43% |
| Brevicon | .5 mgm. NET .035 mgm. EE | 10.5 mgm. NET .735 mgm. EE | 33% | −13% |
| Loestrin 1.5/30 | 1.5 mgm. NET .03 mgm. EE | 31.5 mgm. NET .63 mgm. EE | 22% | 62% |
| Norlestrin 21, 1/50 | 1.0 mgm. NET .05 mgm. EE | 21.0 mgm. NET 1.05 mgm. EE | 53% | 43% |
| Norlestrin 21, 2.5/50 | 2.5 mgm. NET .05 mgm. EE | 52.5 mgm. NET 1.05 mgm. EE | 53% | 77% |

While progestin, norethindrone and norethindrone acetate, administered in Examples I and VI is greater than that of norgestrel administered by Lo/Ovral, it is documented that norgestrel is biologically substantially (30 times) more active than norethindrone acetate. (See: Dialogues in Oral Contraception, Vol. 1, No. 1, November, 1975, page 5) Comparing the pharmacological dosage strength of progestin over the cycle, the follicular luteal administration also provides a substantially reduced, in terms of pharmacological activity, dosage of progestin as well.

Although Loestrin 1/20 provides a lower total dose of ethinyl estradiol during the cycle than Examples I and VI, the Examples provide a 43% reduction in progestin administered. Even more importantly, in Loestrin 1/20 ethinyl estradiol is given continuously and always in combination with a high dose of norethindrone acetate. Further Loestrin 1/20 allows for only a seven day recovery period from exogenous estrogen and progestin. Loestrin 1/20 permits unpredicatable suppression in and escape of endogenous estrogen and has a significantly lower continuation rate when compared with the Examples because of significant problems with breakthrough bleeding. More important, each example of the present invention provides a substantially larger target organ rest period from exogenous estrogen and from a significant exogenous progestin dosages as well as from combination dosages.

Comparison of total cycle dosages of other Examples with other combination formulations yields similar significant reductions achieved for comparable dosage systems.

While efficacy and side effects resulting from the administration of any steroid formulation depend upon the clinical state of the patient, it is significant that in comparison with available combination pills formulated from the same steroids as the Examples, the folicular luteal formulations reduce the total dosage of exogenous steroids administered and provides both efficacy, menstrual cycle control, and a more acceptable level of side effects, clinical, endocrine, and metabolic.

EXAMPLE VIII

This formulation is depicted in FIG. 6 at 28. Daily dosage, beginning with the first day of a menstrual period is as follows:

| Segment Days | Day | Daily Dosage |
|---|---|---|
| Follicular stage | | |
| 3 | 1 through 3 | No exogenous steriods. |
| 5 | 4 through 9 | .25 mgm. Ethinyldiol Diacetate |
| 6 | 10 through 16 | .25 mgm. Ethinyldiol Diacetate and |
| | | .02 mgm. Ethinyl Estradiol |
| Luteal Stage | | |
| 14 | 17 through 30 | 1.0 mgm. Ethinyldiol Diacetate and |
| | | .05 mgm. Ethinyl Estradiol |

Total Cycle Dosage:
16.75 mgm. Ethinyldiol Diacetate
.82 mgm. Ethinyl Estradiol

This follicular luteal system is for administration to prevent unplanned pregnancies and breakthrough bleeding while reducing the dose of estrogen and progestin. In FIG. 6, this follicular-luteal formulation, 28, is depicted in comparison with the accumulated and daily dose of estrogen and progestin of Lo/Ovral 1/20 at 32, and "Demulen" (0.05 mgm. ethinyl estradiol and 1.0 mgm. ethinyldiol diacetate for twenty one days) at 31 and with the normal range of endogenous estrogen, 30. The designated arbitrary corpus luteum was fourteen days and there was minimal breakthrough uterine bleeding. The first arbitrary follicular phase relied on low dose progestin with no exogenous estrogen pre-ovulatory. Ten thousand treatment cycles revealed virtually no unexpected pregnancies and minimal breakthrough bleeding.

The formulation of Example VIII delivers smaller amounts of progestin during the first half of the follicular phase of the cycle. Small doses of exogenous estrogen and progestin are given in combination in the second half of the follicular phase of the cycle. Increased amounts of progestin and estrogen are administered during the luteal half of the cycle when these hormones would normally be secreted by a functioning corpus luteum. The side effects associated with prolonged administration of combination oral contraceptives and a sustained suppression of the hypothalmous and pituitary as well as high dose continuous exposure of the liver to exogenous estrogen and progestin are thus circumvented. In the formulation of Example VIII, a small dose of progestin by itself is administered for least five to seven days without breakthrough bleeding.

A three-day period without any exogenous steriod and five days of progestin alone provides eight days in the synthetic cycle without exogenous estrogen. A small buildup of combination low dose estrogen/progestin for the following six or seven days enables the dose of the combination estrogen/progestin to be cut significantly. In the luteal phase, the dosage administered for fourteen days is associated with very little breakthrough bleeding and, in fact, is associated with less breakthrough bleeding than Demulen given for twenty-one days; menstrual cycle performance on bleeding analysis was better than Demulen by itself and equal to Ovulen, (0.1 mgm. mestranol, 1.0 mgm. ethynodiol diacetate for 20, 21 days) which is a significantly more potent estrogen/progestin formulation.

The advantage of the formulations of the present invention are that a pharmacologically effective steriod contraceptive is obtained with a substantially reduced dosage of exogenous steriods. In comparison with Demulen which uses the same exogenous estrogen and progestin but an altered formulation, Example VIII provides a 20% reduction in the amount of the progestin component, Ethinyldiol Diacetate, and a 22% reduction in the amount of the estrogen component, Ethinyl Estradiol. In comparison with the performance of Demulen the complaints reported with the formulation of Example VIII were as follows:

| | Demulen | Example VIII |
|---|---|---|
| Total number of patients | 975 | 448 |
| Number of cycles | 10,839 | 8403 |
| Number of patients complaining | 344 | 68 |

The pregnancy rate for Example VIII stands at 1.1/100 women/years and the current Demulen pregnancy rate is 0.87/100 women/years. In comparison of clinical and metabolic side effects, Example VIII with its significantly reduced steroid dosage and Demulen were approximately similar.

In addition to providing a lower total dosage of exogenous steroids and having an acceptable pregnancy rate and side effects, Example VIII also provides a minimal incidence of breakthrough bleeding and a prompt return of ovulation in the patients studied.

EXAMPLE IX

This formulation is depicted in FIG. 6 at 29. Daily dosage, beginning with the first day of the menstrual period is as follows:

| Segment Days | Day | Daily Dosage |
|---|---|---|
| | Follicular stage | |
| 3 | 1 through 3 | No exogenous steriods. |
| 12 | 4 through 15 | .35 mgm Norethindrone |
| | Luteal stage | |
| 6 | 16 through 21 | .35 mgm. Norethindrone .02 mgm. Ethinyl Estradiol |
| 7 | 22 through 28 | .5 mgm. Norethindrone .035 Ethinyl Estradiol |

Total Cycle Dosage:
9.8 mgm. Norethindrone
.365 mgm. Ethinyl Estadiol

This example provides the lowest total estrogen dose and the least number of days of estrogen administration in the treatment cycle of the follicular-luteal method which still has borderline acceptable menstrual cycle control. The estrogen content was 13% less than Loestrin 1/20, the lowest dose combination estrogen/progestin. Some endometrial breakthrough bleeding occurred in the arbitrary corpus luteum phase of the treatment cycle on the last seven days of estrogen/progestin as well as late in the six days of lower dose combination estrogen/progestin. There was also some breakthrough bleeding in the arbitrary follicular phase but it was inconsequential.

This Example is imperfect for good cycle control; however, treatment cycle estrogen has been reduced to an irreducible low level. No pregnancies occurred and metabolic parameters appeared satisfactory. Example IX establishes the lower limits of exogenous estrogen reduction both in the Follicular and Corpeus Lutem phase of the treatment cycle if breakthrough bleeding is to be minimized.

This formulation demonstrates that Follicular-Luteoal formulations can be used just as effectively with any progestin. The readily available, Norethindrone was used. Norethindrone was administered by itself in the first half of the cycle. Twelve days of low dose progestin by itself was too long; nine days of low dose progestin by itself was superior to twelve in minimizing breakthrough bleeding. Formulations of previous examples which provide a five to seven day low dose progestin are superior, however, to nine days in the prevention of breakthrough bleeding.

Here, an intermediate or low dose of combination estrogen/progestin was administered in the early corpus luteum phase. This was not associated with significant breakthrough bleeding. Periods of administration of low dose estrogen/progestin varied from five to ten days. Menstrual performance was satisfactory with five days of such administration; however, breakthrough bleeding became more of a problem after five to seven days of low dose estrogen/progestin.

Combination estrogen/progestin for the thirteen day corpus luteum was tried in various doses: doses of estrogen at 0.035 mgm.; and doses of a moderate strength progestin at 0.5 mgm. "Modicon" was more frequently associated with breakthrough bleeding after seven to ten days, than with Northindrone, 1 mgm. and Ethinyl Estradiol 0.05 mgm. for seven days.

Hence, pharmacologically weaker progestins had to be used in larger doses with low dose estrogen to prevent corpus luteum breakthrough bleeding. Also corpus luteum Ethinyl Estradiol in combination with moderately biologically potent progestins should exceed 0.035 mgm. if breakthrough bleeding is to be minimized as FSH and LH suppressed.

Further, the longer adequate dose estrogen/progestin was administered the longer the latent period for withdrawl bleeding after the combination was stopped.

In the formulation of this Example, the dose and the length of time exogenous estrogen is administered during the cycle was reduced to an irreducible low, if the endometrial lining of the uterus was to remain intact. However, by lengthening the progestin administration thus encouraging endogenous FSH and estradiol 17B and reducing the dose of the corpus luteum progestin/estrogen, cycle control becomes unsatisfactory and breakthrough bleeding was a significant clinical problem.

Notwithstanding, the incidence of breakthrough bleeding, the formulation of this example provided effective contraception and the incidence of breakthrough bleeding was comparable to that experienced with other available low dose pills.

In contrast to "Brevicon" which is formulated with the same steriods a Example IV, the reduced dosage of Example IX is considerable.

| | Daily Dosage | Total Cycle Dosage | Reduction Achieved by Example IX |
|---|---|---|---|
| Brevicon | .035 Ethinyl mgm. Estradiol | .735 mgm. | 50% |
| | 0.5 mgm. Norethindrone | 10.5 mgm. | 7% |

EXAMPLE X-A

Figure 7:
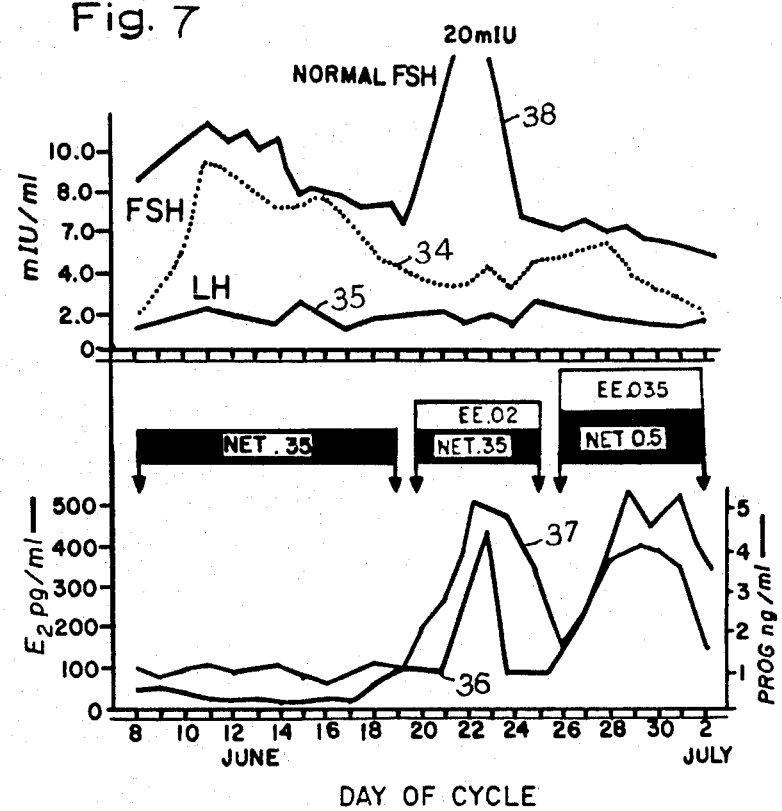
FIG. 7 depicts the daily alteration in serum FSH, LH, estradoil 17B, and progesterone found in a Euestrogenic normal ovulatory patient who was administered a Follicular Progestin Luteal Replacement Formulation of the invention for approximately one year. Note the lack of total suppression of endogenous FSH, LH, estradiol 17B, and progesterone in contrast with FIG. 3 and FIG. 4.

FIG. 7 depicts a cycle of daily serum FSH, 34, LH, 35, estrogen, 36 and progesterone, 37, in a euestrogen patient treated for one year with the formulation of Example IX. Normal FSH is at 38. The low dose unopposed progestin in the arbitrary follicular phase is associated with FSH stimulation, or at least the absence of FSH suppression. This provides for early follicular phase folliculogenesis without evidence of endogenous estrogen production. Not until low dose combination estrogen/progestin is administered in the beginning of the corpus luteum phase is endogenous estrogen elaborated, the estradiol reaching 350 to 450 pg/ml. The assay used does not measure the exogenous synthetic estrogen.

It is submitted that the early developing follicles in the presence of endogenous LH released during the low dose combination estrogen/progestin is responsible for the endogenous estrogen that appears in the early portion of the arbitrary corpus luteum. This endogenous estrogen gradually decreases when the low dose estrogen/progestin is stopped and higher dose combination estrogen/progestin is initiated. Endometrial breakthrough bleeding in Example IX is coincident with this fall in endogenous estrogen even though exogenous ethinyl estradiol, 0.035 mgm., and norethindrone, 0.05 mgm., are simultaneously administered. This inappropriate elaboration of endogenous estrogen is corrected by either shortening the number of days of administration of low dose progestin only to allow for post-antral follicle development, or to reduce low dose estrogen/progestin (EE 0.02 mgm.; NET 0.35 mgm.)) from seven to four or fewer days to minimize endogenous LH release and subsequent ovarian estrogen production. Another adaptation would be to increase the number of days of the higher dose estrogen/progestin given during the final days of the arbitrary corpus luteum.

EXAMPLE X-B

Figure 8:
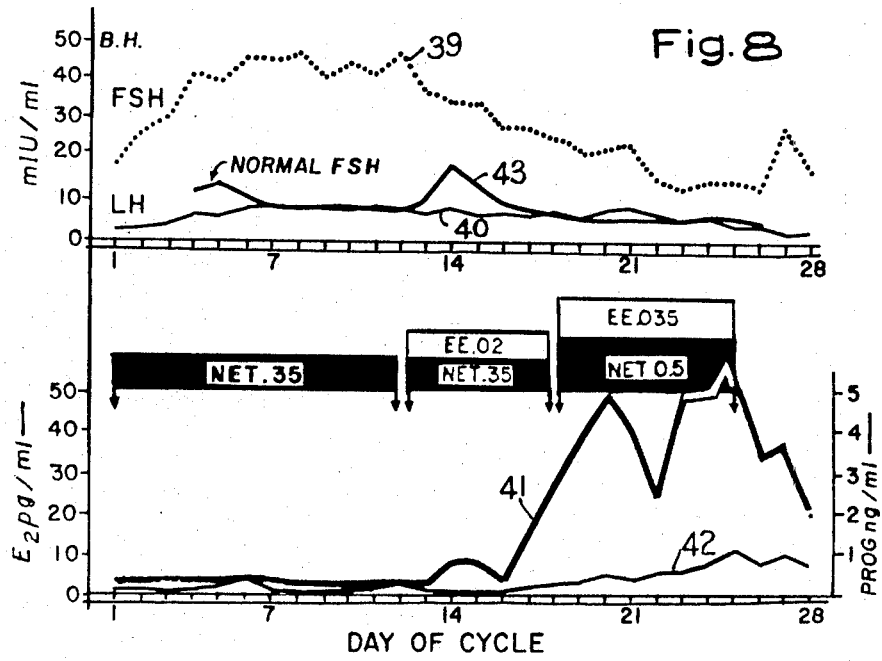
FIG. 8 depicts the daily alteration in endogenous FSH, LH, estradoil 17B, and progesterone in a hypoestrogenic patient who was administered a Follicular Progestin Luteal Replacement Formulation of the invention for one year, in illustration of the necessity for patient selection in the administration of the Follicular Estrogen/Progestin Luteal Replacement Formulations of the present invention.

FIG. 8 depicts a hypoestrogen cycle in a 47 year old female treated for one year with a modified Follicular-Luteal Replacement of Example IX whose control follicular phase FSH is elevated and endogenous estrogen below 20 pg/ml. FSH is 39; LH, 40; estrogen, 41; and progestin 42. Normal FSH is at 43. After treatment there is minimal estrogen in the arbitrary follicular phase and only an elevation of endogenous estrogen to 50 pg/ml after early arbitrary corpus luteum low dose combination estrogen/progestin for 7 days, and similar levels of endogenous estrogen when ethinyl estradiol, 0.035 mgm., and norethindrone 0.5 mgm. were administered for the terminal seven days of the arbitrary corpus luteum.

The difference between this clinical situation and that described in Example X-A points up the need for patient selection and the physiologic fact that a given combination estrogen/progestin is not appropriate for all clinical situations.

Hence the present invention offers flexibility in management of the normal and abnormal menstrual cycle by treating follicular phase and luteal phase independently with a different sex steroid, i.e., exogenous estrogen or progestin during days Seven through Fourteen. In almost all clinical situations a standardized arbitrary corpus luteum is appropriate, but this is not true of the second half of the follicular phase. Thus, compared with the "normal" in FIG. 1, the patient in FIG. 8 requires exogenous estrogen in the second half of the follicular phase since secondary ovarian failure (impending menopause) precludes endogenous production of estrogen. Whereas, progestin from day Seven to Fourteen is follicular-luteal phase sex steroid replacement's basic formulation for euestrogenic and hyperestrogenic menstrual cycles, estrogen substitution in the second half of the arbitrary follicular phase is necessary for treatment of the hypoestrogenic patient and embodies a completely new therapeutic concept in sex steroid management not only for contraception in various age groups, i.e., post puberty, adolescent, reproductive years, and climacteric, but also the menstrual dysfunction patient.

EXAMPLE XI

In connection with the clinical use of follicular-luteal replacement methods and formulations of the present invention, patient selection, including an evaluation of a particular patient's clinical state must be made and the appropriate formulation prescribed.

For example, for the "normal" euestrogen patient desiring contraception and pregnancy spacing, in most instances the formulation of Example I will provide the benefits of the invention incident with a substantial reduction in estrogen over combination dosages without further need for therapeutic manipulation of the menstrual cycle. If subsidiary clinical problems occur as the result of the contraception or pregnancy spacing use of the formulations of the invention, then the various adaptation of the Examples for presenting clinical states and problems encountered may be employed depending on the presenting estrogen state of the patient.

While Example I of the follicular-luteal sex steroid replacement will attain good cycle control 75% of the time, the five other pharmacologic alterations of Examples II, III, IV-A, IV-B and V are categorized for specific clinical situations. Two pregnancies have occurred in these formulations in over 10,000 treatment cycles. (Both patients omitted pills.) These six formulations are suitable for most clinical presenting states and avoid the necessity for twenty-four different combination estrogen/progestins, of which all but three or four provide excessive doses of estrogen or estrogen/progestin resulting in clinical, endocrine, and metabolic adverse consequences.

EXAMPLE XI-A

Euestrogen Hyperestrogen Alternatives

For the euestrogen or hyperestrogen presenting patient, the follicular-luteal formulations of Examples I, III, IV-A and IV-B are the preferred alternatives.

The follicular-luteal system of Example I represents the lowest dose of total estrogen with the longest rest period from exogenous estrogen. It represents the maximum amount of low dose combination feasible in the early and terminal portion of the corpus luteum. The continuation rate looks to be 65%. The clinical problem of consequence is breakthrough bleeding and menstrual cycle control. The follicular-luteal system of Example IV-A is a treatment for breakthrough bleeding on the follicular-luteal system of Example I. Follicular-luteal systems of Examples II, III and IV-B provide for estrogen priming of the endometrium in the follicular phase and are also for management of breakthrough bleeding with follicular-luteal systems of Examples I, IV-A and V. Improved menstrual cycle control is obtained in follicular-luteal system of Examples III and IV-B by priming the follicular phase endometrium with unopposed exogenous estrogen, decreasing the number of days of early corpus luteum low dose combination (which minimizes endogenous estrogen), lengthening and/or increasing the dose of exogenous estrogen/progestin mid arbitrary corpus luteum, and limiting terminal low dose estrogen/progestin.

EXAMPLE XI-B

Hypoestrogen Alternatives

Because the hypoestrogen patient presents with different physiological needs, follicular luteal systems of steroid dosage are provided for this state. Thus, the follicular-luteal system of Example V is designed for clinical states associated with hypoestrogen. Specifically oligomenorrhea, secondary amenorrhea, and the climacteric state are best managed with follicular phase estrogen replacement. Example V provides endogenous estrogen in the late follicular and low dose estrogen/progestin in the early luteal phase of the cycle; but has been associated with some luteal phase breakthrough bleeding. The follicular-luteal systems of Example II and III supply follicular phase unopposed exogenous estrogen to minimize luteal phase breakthrough bleeding, and maximize menstrual cycle control. The follicular-luteal system of Example IV-B is the best balanced but highest dose replacement regimen to provide follicular phase unopposed estrogen, endometrial priming, and a substantial estrogen/progestin replacement in the corpus luteum phase to maximize menstrual cycle control.

EXAMPLE XII

For the treatment of the dysfunction patient, however, proper diognosis should be made for selection of the appropriate follicular luteal system. Prior to treatment of the anovulatory patient disease or endocrinopathy, should be excluded. It should further be established whether menstrual cycle derangement is ovulatory or anovulatory. If, the latter prevails, is it transient or persistent?

EXAMPLE XII-A

Primary amenorrhea is not the only menstrual dysfunction state associated with hypoestrogenism-hypo or hyper-gonadotropism. Table A chronicles anovulatory patients whose persisting complaints may be oligomenorrhea, hypomenorrhea, or secondary amenorrhea.

TABLE A
ANOVULATION - CLINICAL CLASSIFICATION HYPOESTROGENISM - HYPO OR HYPERGONADOTROPISM (HYPOMENORRHEA, OLIGOMENORRHEA, 2° AMENORRHEA)

I. Status post a reproduction event, i.e., pregnancy, lactation, abortion
II. Pernicious weight loss, including anorexia nervosa
III. Emotional and/or psychogenic stress
IV. Iatrogenic - combination oral contraceptives, depot sex steroids tranquilizers, tricyclics, reserpine
V. Hyperprolactinemia with or without galactorrhea
VI. Premature onset menopause Management of the hypoestrogen patient depends on the short and long term intentions for procreation. Certainly reproduction is unobtainable in such hypergonadotropic states as gonadal dysgenesis and feminizing testicular syndrome. It is mandatory that pituitary tumor be excluded or excised before ovulation stimulation and subsequent pregnancy ensue.

Therapy should be directed toward ovulation induction agents if pregnancy is desired. Reinforcing the CNS-hypo-thalamicpituitary-ovary maturation centers is important for future procreation. Such maturation is associated with chronologic and skeletal age and also the initiation of a proper sex hormone milieu. It has long been recognized that combination estrogen/progestins produce sustained FSH, LH suppression with varying and unpredictable recovery. However, estrogen/progestins in accordance with the invention are administered by a method and in a formulation that is less contraphysiologic for post treatment ovulation. The following physiologic principles that regulate negative and positive gonadotropin feedback response in the normal ovulatory cycle are utilized in accordance with the invention in estrogen/progestin replacement of Example II for the treatment of the hypoestrogenic-hypogonadotropic individuals.

1. No exogenous estrogen or progestin during day One through day Seven in the follicular phase of the cycle to allow for FSH recovery.

2. Unopposed low dose estrogen during day Seven through day Fourteen to minimize FSH suppression and allow for tertiary follicle development and endometrial priming.

3. Unopposed low dose estrogen (ethinyl estradiol 0.02 mgm.) during day Seven through day Fourteen permits LRF synthesis and release and initiates sensitization of pituicyte to LRF.

4. Unopposed low dose estrogen during day day Seven through day Fourteen permits pituitary synthesis and storage of LH, defers LH midcycle release, accentuates the potency of exogenous progestin at the end organ.

5. Short term low dose estrogen (ethinyl estradiol 0.02 mgm) on day Fifteen through day Eighteen concurrent with low dose progestin (norethindrone, 0.35 mgm.) allows for follicular development, luteinization of theca interna and endogenous production of E2.

6. Short term adequate exogenous estrogen (ethinyl estradiol 0.05 mgm) and concurrent short term exogenous progestin, (norethindrone acetate, 1 mgm.) during day Nineteen through day Twenty-five allows for predictable, short term, and reversible FSH, LH suppression.

7. Short term low dose exogenous estrogen (ethinyl estradiol, 0.02 mgm.) and concurrent short term exogenous progestin, (norethindrone 0.35 mgm.) during day Twenty-six through day Twenty eight are administered terminally to initiate prompt withdraw bleeding and hypothalamic-pituitary recovery of FSH.

Such a replacement estrogen/progestin regimen is reasonable therapy for the hypoestrogen-hypogonadotropic individual with menstrual dysfunction secondary to anovulation. This is especially true since many individuals do not seek immediate pregnancy, anticipate future procreation, and in fact look for menstrual regulation and interim effective contraception. The advantage of Follicular-Estrogen/Luteal Replacement (FELR) or supplementation is menstrual cycle regulation; prompt recovery by hypothalamus and pituitary post exogenous estrogen/progestin exposure, diminished threat to future ovulation, and minimization of long term metabolic adverse consequences of high dose combination estrogen/progestin.

EXAMPLE XII-B

EUESTROGENIC-HYPERESTROGENIC-TONIC FSH, LH-FAILURE CYCLIC LH

In the adolescent years or the reproduction era menstrual dysfunction may be associated with abnormal ovulatory cycles or anovulation. The euestrogen and hyperestrogen state with tonic FSH, LH and failure of cyclic LH may be transient or persistent. Invariably there is some problem in orderly, progressive folliculogenesis but follicular development and luteinized theca interna are certainly in evidence.

TABLE B
ANOVULATORY CLINICAL CLASSIFICATION EUESTROGENIC-HYPERESTROGENIC-TONIC FSH, LH-FAILURE CYCLIC LH (HYPERMENORRHEA, MENORRHAGIA, POLYMENORRHEA, OLIGOMENORRHEA, 2° AMENORRHEA WITH PROGESTERONE WITHDRAWAL)

I. Status post reproduction event, i.e., pregnancy, lactation, abortion, sterilization.
II. Obesity - peripheral conversion androstenedione to estrone.
III. Emotional and/or psychogenic stress.
IV. Iatrogenic - status post minipill, depot progesterone, indiscriminate exogenous estrogen, status post combination estrogen/progestin, tranquilizers, tricyclics.
V. Ovarian - functional cysts, multiple follicular ovary, steinoid ovary, Stein-Leventhal syndrome, granulosa-theca tumor.
VI. Endocrinopathy - thyroid, adrenal.

Diagnostic procedures are similar to hypoestrogen-hypogonadotropin patients although management differs. These patients withdraw from progesterone (Prolutin) have tonic and circhoral FSH and LH rhythm, and usually respond to exogenous estrogen challenge (EE 0.04×5) with a positive LH feedback response. Most respond to a trial of Clomid, those that fail should be evaluated for hyperprolactinemia and other subtle endocrinopathies, i.e., hyperandrogenism, PCOS, thyroid, adrenal, and hypothalamic-pituitary endocrinopathies. Management of these patients with repetitive Clomid or Clomid plus estrogen, APL, or Pergonal or repetitive ovulation stimulation with human menopausal gonadotropin (HMG) or human pituitary gonadotropin (HPG) with or without human chorionic gonadotropin (HOG) is not practical unless conception is desired. Therefore, such patients require an estrogen/progestin replacement pattern adequate for menstrual cycle control and one that will not adversely affect future ovulation either spontaneous or induced. An alternate follicular-luteal estrogen/progestin replacement regimen is utilized in patients who are anovulatory but bleed spontaneously or who withdraw bleed from exogenous progesterone. The formulation of the invention embodies the same physiologic and pharmacologic principles that appear in the design of Follicular-Estrogen/Luteal Replacement (FELR) in the hypoestrogen-hypogonadotropin patient: however, progestin is administered from day Seven to day Fourteen in Follicular-Progestin/Luteal Replacement (FPLR) of Example I in the euestrogen or hyperestrogen patient and has the following important dose, ratio, and temporal features:

1. No exogenous estrogen or progestin day One through Seven of the treatment cycle provides for FSH and LH recovery.

2. Unopposed low dose progestin, (norethindrone 0.35 mgm) for day Seven through day Fourteen of the treatment cycle. This anti-estrogen provides for FSH recovery and continued release.

3. Unopposed low dose progestin for day Seven through day Fourteen permits pituitary synthesis and storage of LH, blunts LH midcycle release.

4. Short term low dose estrogen (ethinyl estradiol, 0.02 mgm.) concurrent with low dose progestin (norethindrone, 0.35 mgm) during day Fifteen through day Eighteen allows for follicular development, luteinization of theca intena.

5. Low dose exogenous estrogen (ethinyl estradiol 0.02 mgm) concurrent with low dose progestin (norethindrone, 0.35 mgm.) during day Fifteen through day Eighteen. Such estrogen/progestin ratios are associated with the production of endogenous estradiol (for five to seven days) attaining a serum level of 200–500 pg/ml which initiates LH positive feedback.

6. Short term adequate exogenous estrogen (ethinyl estradiol, 0.05 mgm) and concurrent short term exogenous progestin, (norethindrone acetate, 1 mgm) during day Nineteen to day Twenty-five allows for predictable short term reversible FSH, LH suppression.

7. Short term low dose exogenous estrogen (ethinyl estradiol, 0.02 mgm) and concurrent short term exogenous progestin (norethindrone acetate 0.35 mgm.) for day Twenty-six through day Twenty-eight administered terminally for prompt withdraw bleeding and hypothalamicpituitary recovery of FSH.

Under the Follicular-Luteal Estrogen/Progestin Replacement regimens for hypoestrogen and euestrogen or hyperestrogen patients, reasonable levels of tonic FSH and LH are maintained with a modicum of pulsatile activity and sufficient unopposed exogenous or endogenous estrogen in the latter half of the follicular or early part of the luteal phase to initiate and/or stimulate the estrogen dependent positive LH feedback response.

EXAMPLE XII-C

There are other common clinical situations that mitigate therapeutic flexibility not possible with prior art such as combination estrogen/progestin. Many oligomenorrhea, secondary amenorrhea patients do not have hypoestrogenism but have hyperestrogenism. Hyperestrogen patients may have polymenorrhea, menorrhagia, hypermenorrhea or menometrorrhagia. Such patients are anovulatory and prior art is contraphysiologic as it aids and abets an already deranged hypothalamic-pituitary axis. Irregular bleeding patients should be stopped promptly and predictably by using the arbitrary corpus luteum FSH, LH suppressive dose and endometrial maintenance dose three times daily for seven days. (Bleeding will stop and a withdraw period will ensue within one week). This patient, the hyperestrogenic oligomenorrhea, or secondary amenorrhea, anovulatory patient, will be cycled with follicular-luteal system of Example IV-B to ensue cycle control and withdraw bleeding for a short period of time (3–6 months). She will then be reduced to a more appropriate low dose follicular-luteal formulation, i.e., Example I or Example II if in fact her original problem was spontaneous uninterrupted endogenous hyperestrogenism.

EXAMPLE XII-D

The problem of breakthrough bleeding is a major deterrent to the satisfactory continuation rate with prior art. This is especially true of the low dose combination estrogen/progestins with the single exception of Lo/Ovral. Furthermore the clinical management of breakthrough bleeding with prior art is pharmacologically contraphysiologic, i.e., double the dose of the estrogen/progestin on which breakthrough occurred, change to a biologic more potent pill (estrogen dominant Enovid, progestin-androgen dominant Ovral), dilation and curettage, or hysterectomy. The pathophysiology of spontaneous irregular bleeding or breakthrough bleeding on prior art involves inappropriate priming of the endometrium and pharmacologic overdoses of simultaneous exogenous estrogen and progestin maturation and subsequent predictable dissolution of the endometrium occurs. The administration of combination estrogen/progestins overstimulates the endometrial components, glands, stroma, and vasculature, thus taking it out of phase and ultimately initiating an exhausted atrophic state. Although hypomenorrhea may ensue, all too often breakthrough bleeding or amenorrhea occurs. Prior art makes no reasonable provisions for transient or long-term management of oral contraceptive induced hypomenorrhea (which many consider salutory), oligomenorrhea, breakthrough bleeding or secondary amenorrhea. Follicular-luteal replacement can easily be programmed to adjust to these untoward bleeding patterns. Follicular-luteal systems of Examples II, III and IV-A and IV-B are designed for such contingencies. Follicular phase unopposed estrogen primes the endometrium in follicular-luteal systems of Examples II, III, IV-B and V. Early corpus luteum low dose combination estrogen/progestin has been shortened to two days in follicular-luteal systems of Examples III and IV-B to minimize the ovarian synthesis and release of endogenous estrogen whose withdrawal is coincident with arbitrary corpus luteum breakthrough bleeding.

Further, Example IV-B has increased doses of estrogen/progestin mid arbitrary corpus luteum (day Seventeen to day Twenty-six) to more adequately maintain the endometrium in the second half of the menstrual cycle. The follicular-luteal replacement systems allow for transient threatment of about three to six months for of breakthrough bleeding without changing the drug or resorting to prolonged, excessive, estrogen/progestin target cell exposure. Thus follicular-luteal replacement with very minor dosage changes has provided for a continuing clinical problem in combination estrogen/progestin administration, i.e., breakthrough bleeding and secondary amenorrhea.

EXAMPLE XIII

Like currently available oral contraceptive steroid formulations, follicular luteal formulations for oral administration will be assembled in a unitary package containing daily dosage tablets of appropriate pharmacological strengths in the temporal and dosage interrelationships required for at least one steroid administration cycle. One such package comprising a steroid drug delivery system for oral administration of tablets for one cycle is depicted in FIG. 9, showing the system adapted for the Follicular-luteal method of Example I. The system includes twenty eight tablets in a dispenser in an orderly arrangement to insure temporal and dosage interrelationships in daily tablet administration throughout the twenty eight day drug cycle. In a dispensing package, the steroids are arranged as follows in accord with Example I:

| Number of Tablets | Formulation | |
|---|---|---|
| | Follicular phase | |
| 7 | (early) | Optional: None, pharmacologically acceptable placebo, or iron (ferrous fumarate), 75 mgm.) |
| 7 | (late) | .35 mgm Norethindrone |
| | Luteal phase | |
| 4 | (early) | .35 mgm Norethindrone .02 mgm Ethinyl estradiol |
| 7 | (mid) | 1.0 mgm Norethindrone acetate and .05 mgm. Ethinyl estradiol |
| 3 | (late) | .35 mgm Norethindrone and .02 mgm Ethinyl estradiol |

The first seven tablets 44 through 50, are optional, however, in conventional administration, tablets are administered beginning with the onset of menstruation, an easily identifiable occurrence in the cycle, to reduce error in beginning the pharmacologically potent dosages of steroids. As in conventional use, if included, the first seven tablets may be either a pharmocogically acceptable placebo or iron. These are dispensed one per day for each of the first seven days of the drug administration cycle during the first half of the follicular phase.

Beginning the steroid dosage, seven tablets, 51 through 57, each formulated with 0.35 mgm norethindrone follow, if the optional first seven tablets are included. They are separately administered, one per day during the late, second half, of the follicular phase of Example I.

These are followed by tablets formulated to provide the appropriate steroid dosage of Example I during the luteal phase. For the early segment of the luteal phase, four tablets, 58 through 61, formulated with 0.35 mgm. norethindrone and 0.02 mgm. ethinyl estradiol are provided. For the mid luteal phase, seven tablets, 62 through 68, with 1.0 mgm. norethindrone acetate and 0.05 mgm. ethinyl estradiol, and for the terminal portion of the luteal phase, three tablets, 69 through 71, of 0.35 mgm. norethindrone and 0.02 mgm. ethinyl estradiol follow. If ordered in this manner in a package and taken by the patient one tablet per day, the delivery system will provide sex steroids in the temporal and dosage relationships required by Example I.

It is apparent that tablets may be formulated and ordered in a unitary package for one cycle's dosage in a similar manner in accordance with other examples of the invention. For convenience, the following chart sets forth in summary fashion the appropriate temporal order, dosage interrelationships and tablet formulation of the Examples. For the various follicular and luteal segments the chart indicates relative dosage levels as: LD=low or small dose; RD=Regulation or adequate dose; DD=Diminished dose, i.e., reduced from regulation, or low dose. Increased dosage of progestin is indicated by 2xP in the formulation. Above the relative dosage level, the number of tablets required for each segment of the cycle is provided. Beneath, the formulation is described: E denotes estrogen; P, progestin and E/P is combination estrogen and progestin. The "optional" tablets, indicated by O, may be placebo or iron.

| | Follicular-Luteal Cycle Tablet Dosage and Order Number of Tablets Relative Dosage Level Formulation | | | | |
|---|---|---|---|---|---|
| | Follicular Tablets | | | Luteal Tablets | |
| Example | (early) First Tablet | (late) | (early) | (mid) | (terminal) Last Tablet |
| I. | 7 | 7 | 4 | 7 | 3 |
| | 0 | LD | LD | RD | DD |
| | | P | E/P | E/P | E/P |
| II. | " | 7 | 4 | 7 | 3 |
| | | LD | LD | RD | DD |
| | | E | E/P | E/P | E/P |
| III. | " | 7 | 2 | 10 | 2 |
| | | LD | LD | RD | DD |
| | | E | E/P | E/P | E/P |
| IV-A. | " | 7 | 2 | 10 | 2 |
| | | LD | LD | RD | DD |

-continued

Follicular-Luteal Cycle Tablet Dosage and Order
Number of Tablets
Relative Dosage Level
Formulation

| Example | Follicular Tablets | | | Luteal Tablets | |
|---|---|---|---|---|---|
| | (early) First Tablet | (late) | (early) | (mid) | (terminal) Last Tablet |
| IV-B. | " | P | E/P | E/2×P | E/P |
| | | 7 | 2 | 10 | 2 |
| | | LD | LD | RD | DD |
| | | E | E/P | E/2×P | E/P |
| V. | " | 7 | 7 | | 7 |
| | | LD | LD | | RD |
| | | E | E/P | | E/P |
| VI. | " | 7 | 7 | | 7 |
| | | LD | LD | | RD |
| | | P | E/P | | E/P |
| VIII. | 3 6 | 6 | | 14 | |
| | 0 LD | LD | | RD | |
| | E | E/P | | E/P | |
| IX. | 3 | 12 | 6 | | 7 |
| | 0 | LD | LD | | RD |
| | | P | E/P | | E/P |

In another view of a tablet package depicted in FIG. 9A, B, C, individually formulated tablets may be maintained in individual slot recesses, separate from one another, each recess adapted to hold one tablet. The tablets are formulated and in circular order in accordance with a predetermined follicular luteal system. The beginning tablet of the steroid administration cycle is appropriately indicated. The package consists of a circular body, 72, in which the individual recesses, such as indicated by 73, for each pill are formed in the first body element, 74, which is covered by a rotating cover 75, having one slot, 76, for the dispensation of one pill from a recess at a time. The dispensing slot is rotated by means of a ratchet lever, 77, communicating by protrusion 78 with corresponding segmented indentations 79 in the cover and a spring return device, 80. The ratchet rotates the cover in one direction only and allows the dispensation of one pill only per time, per segment in the order required, one pill per day.

In this manner, the order of tablet administration is insured. As the tablets are ordered and formulated in accordance with the appropriate follicular luteal prescription, the proper tablet with the appropriate formulation and potency will be dispensed on the right day in its appropriate required order in the drug cycle. Correspondingly, on the inner-rim of the container, the days of the week may be inscribed so that the patient, once the beginning day is co-ordinated with the beginning of the drug cycle, may verify the proper day upon which a particular pill should be taken once the drug cycle has begun.

The specific package depicted is not an element of the invention; and there are many other suitable package devices which would be similarly appropriate for use in dispensing tablets in accordance with the invention.

While in the Examples, specific miligram dosages of particular sex steroids are provided to indicate the formulations of individual tablets, pharmacologically equivalent dosages of other steroids may be substituted in equivalent potencies with suitable formulation adjustments determined by the relative potency of the particular steroid substituted with respect to that of the Example. (See: Dialogues in Oral Contraception, Vol. 1, No. 1, February 1976 for chart of relative potency).

EXAMPLE XIV-A

The efficacy of follicular luteal formulations is illustrated in the comparison of the Examples with prior art combination dosages in terms of continuation rates, side effects and complaints of patients receiving such dosages.

In a comparison between the formulation of Example VIII with the formulation of Demulen, each using the same steroid components, Example VIII providing a lower steroid total cycle dosage, yields the following results:

| Study conducted | Demulen | Example VIII |
|---|---|---|
| Total number of patients | 975 | 448 |
| Number of cycles | 10,839 | 8403 |
| Number of patients complaining | 344 | 68 |
| Complaints Reported | Demulen | Example VIII |
| Intermenstrual bleeding | 65 (6.7%)* | 14 (3.6%) |
| Amenorrhea | 45 (4.6%) | 5 (1.0%) |
| Headache | 137 (14%) | 50 (12.7%) |
| Depression | 32 (3.3%) | 16 (4.4%) |
| Dizziness | 18 (1.8%) | 1 (0.2%) |
| GI symptoms | 18 (1.8%) | 6 (1.5%) |
| Vaginal discharge | 20 (1.8%) | 6 (1.5%) |
| Leg pain/swelling | 15 (1.5%) | 9 (2.3%) |
| Backache | 11 (1.1%) | 9 (0.2%) |
| Loss of libido | 21 (2.2%) | 2 (0.5%) |
| Visual complaints | 2 (0.2%) | 1 (0.2%) |
| Thromboembolic | 11 (1.1%) | 1 (0.2%) |
| Breast discomfort | 2 (0.2%) | 4 (1.0%) |
| Cervicitis erosion of cervix | 1 (0.1%) | 6 (1.5%) |

In comparison of continuation rates, results between Demulen and Example VIII in studies are as follows:

| | Demulen | Example VIII |
|---|---|---|
| Involuntary pregnancy | 0.87 ± 0.209 | 1.1 ± 0.58 |
| BTB and/or spotting | 4.37 ± 0.449 | 3.6 ± 0.91 |
| Amenorrhea | 1.51 ± 0.251 | 0.000 |
| Other medical | 11.57 ± 0.692 | 13.1 ± 1.20 |
| Desires pregnancy | 1.98 ± 0.294 | 5.6 ± 0.87 |
| No more need | 1.96 ± 0.307 | 0.7 ± 0.44 |
| Changed to other contraceptive | 2.34 ± 0.340 | 2.0 ± 0.70 |
| Other non-medical | 11.87 ± 0.702 | 3.1 ± 0.96 |
| No reason given or known | 10.52 ± 0.662 | 6.7 |
| Rate of continuation in | | |

-continued

|  | Demulen | Example VIII |
|---|---|---|
| study | 52.0 | 61.6 ± 2.3 |

These results suggest that the formulation of the Example is at least comparable with and may be superior to the prior art combination tablet with the same steroid components.

EXAMPLE XIV-B

The follicular progestin luteal replacement formulation of Example I and the follicular estrogen luteal replacement formulation of Example II achieve the following clinical results among patients presenting as contraceptive (Ct.), climacteric (Clm.) and gynecological problem (Gyn.). All patients combined are also indicated (Comb.)

In this study, patients starting and completing were as follows:

|  | EXAMPLE I | EXAMPLE II |
|---|---|---|
| Patients started: | 367 | 164 |
| Patients cut off: | 152 | 86 |
| Patients discontinuing: | 44 | 27 |
| Medical reasons | 31 | 18 |
| Non-medical | 13 | 9 |

Medical Reasons for discontinuing are set forth below:

|  | EXAMPLE I | | | | EXAMPLE II | | | |
|---|---|---|---|---|---|---|---|---|
|  | Ct. | Clm. | Gyn. | Comb. | Ct. | Clm. | Gyn. | Comb. |
| Breakthrough bleeding | 12 | 1 | 5 | 18 | 5 | 1 | 1 | 7 |
| Amenorrhea | 2 | — | — | 2 | 2 | — | — | 2 |
| Abdominal pain | — | — | 2 | 2 | — | — | — | — |
| Abdominal cramps | 1 | — | 1 | 2 | 2 | — | — | 2 |
| Headaches | — | — | 1 | 1 | — | — | — | — |
| Eye Problems | 1 | — | — | 1 | — | 1 | — | 1 |
| Bloating | 1 | — | — | 1 | — | — | — | — |
| Moody | 1 | — | — | 1 | — | — | — | — |
| Nausea | 1 | — | — | 1 | — | — | 1 | 1 |
| Acne | 1 | — | — | 1 | — | — | — | — |
| Hair loss | 1 | — | — | 1 | — | — | — | — |
| Breast tenderness | — | — | — | — | 1 | — | — | 1 |
| Leg cramps | — | — | — | — | — | 1 | — | 1 |
| Ovulated | — | — | — | — | — | — | 1 | 1 |
| Regulated | — | — | — | — | — | 1 | — | 1 |
| Pregnant | — | — | — | — | 1 | — | — | 1 |

Total number and type of side effects for patients studied is as follows:

|  | Example I | Example II |
|---|---|---|
| Patients Studied: | 100 | 64 |
| Cycles Studied: | 343 | 253 |
|  | Example I Cycles | Example II Cycles |
| Cramps | 39 | 65 |
| Nausea | 27 | 30 |
| Headaches | 26 | 41 |
| Abdominal pain | 15 | 18 |
| Amenorrhea | 13 | 15 |
| Breast tenderness | 9 | 9 |
| Leg pain | 5 | 8 |
| Bloating | 4 | 4 |
| Back Pain | 3 | 10 |
| Acne | 3 | 3 |
| Fluid Retention | 3 | 3 |
| Increased weight | 2 | 2 |
| Dizziness | 1 | 2 |
| Chest pain | 1 | 1 |
| Migraine | 1 | 1 |
| Canker sores | 1 | 1 |
| Depression | — | 2 |
| Eye problems | — | 1 |

As to breakthrough bleeding, results of the Examples are as follows:

|  | Example I | Example II |
|---|---|---|
| Combined total cycles: | 343 | 253 |
| With BTB | 130 | 66 |
| Without BTB | 213 | 187 |

In this compilation of study results, results are indicated by cycle rather than patient. These results verify clinically acceptable performance with a substantially reduced exposure to steroid dosage.

In sum, in the foregoing specification, I have described my invention of the follicular luteal steroid dosage method, formulation and drug delivery system. As is apparent, the invention provides a method to minimize the dose and days of administration of exogenous estrogen in oral sex steroid treatment cycles, a method to minimize the days of combination exogenous estrogen and progestin in oral sex steroid treatment cycles, a method to minimize hepatic, morphologic, metabolic, and endocrine adverse consequences from oral sex steroid treatment cycles, and a method to minimize further ovulation disturbance in patients administered oral sex steroids for menstrual cycle manipulation.

Further, it provides oral sex steroid replacement in pregnancy spacing and contraceptive applications as well as treatment in the management of menstrual irregularity and menstrual dysfunction. The invention allows a rational decrease in exogenous steroids administered, providing a significant reduction with surprising results in efficacy in reduced dosage quantities.

This invention is unique, and addresses itself to the problem of appropriate estrogen/progestin menstrual cycle replacement minimizing the clinical, endocrine, and metabolic side effects of combination estrogen/progestin to which millions of women who take combination estrogen/progestin are currently subjected in gross overdose. It meets the serious problem of overdose with a solution that has eluded the pharmaceutical industry, despite a long felt need and many attempts, for years.

What is claimed is:

1. A treatment method for regulating the menstrual cycle of a presenting patient, the menstrual cycle having a first occurring follicular phase followed by a luteal phase, and the patient having a presenting endogenous estrogen characteristic, comprising:
    (A) determining the presenting endogenous estrogen characteristic of the patient and identifying the patient's presenting endogenous estrogen characteristic as one of (1) euestrogenic, (2) hyperestrogenic, (3) hypoestrogenic;
    (B) administering to the patient effective dosages of pharmacologically active steroid compositions in an ordered temporal succession based on the identified endogenous estrogen characteristic of the patient, in which succession:
(1) during the follicular phase of the menstrual cycle there is:
  (a) a first period of absence of administration of any pharmacologically active steroid composition; and
  (b) a following period of administration of a low dose of one pharmacologically active steroid composition adapted to the identified endogenous estrogen characteristic of the patient and selected from the group of estrogenic active steroids and progestational active steroids; and
(2) during the luteal phase of the menstrual cycle, there is administered an effective dosage of a pharmacologically active composition which comprises a combination of an estrogenic active steroid and a progestational active steroid;
whereby a follicular and luteal phase correspondence is established between the pharmacological activity characteristics of the compositions administered and the menstrual cycle of the patient.

2. The method of claim 1 in which:
(a) the presenting endogenous estrogen characteristics of the patient is identified as one of (1) euestrogenic and (2) hyperestrogenic;
(b) pharmacologically active steroid compositions are administered for from 21 to 25 days in an ordered temporal succession during an approximately 28 day menstrual cycle; and
(c) the follicular phase is approximately 14 to 15 days, during which:
  (i) no composition having a steroid activity is administered for a first approximately 3 to 7 day period; and
  (ii) a dosage of a progestational active steroid composition, equivalent in daily pharmacological activity to about 0.35 mgm. norethindrone by oral dosage, is administered for a following period of approximately 6 to 12 days.

3. The method of claim 2 in which pharmacologically active steroid compositions are administered for approximately 21 days, and the follicular phase is approximately 14 days during which:
(i) no composition having a steroid activity is administered for a first approximately 7 day period; and
(ii) the dosage of the progestational active steroid composition is administered for the following approximately 7 days.

4. The method of claim 1 in which:
(a) the presenting endogenous estrogen characteristic of the patient is hypoestrogenic;
(b) pharmacologically active steroid compositions are administered for approximately 21 days in an ordered temporal succession during an approximately 28 day menstrual cycle; and
(c) the follicular phase is approximately 14 days, during which:
  (i) no composition having a steroid activity is administered for a first approximately 7 day period; and
  (ii) a dosage of an estrogenic active steroid composition, equivalent in daily pharmacological activity to about 0.02 mgm. ethinyl estradiol by oral dosage, is administered for a following period of approximately 7 days.

5. The method of claim 3 or claim 4 in which during the luteal phase the dosage of combined estrogenic active steroid and a progestational active steroid comprises:
(i) an initially low dosage equivalent in daily pharmacological activity to about 0.02 mgm. ethinyl estradiol combined with about 0.35 mgm. norethindrone by oral dosage, for each day for the approximately first 7 days of the luteal phase; followed by
(ii) a dosage of greater estrogenic and progestational activity than the initial dosage, said greater dosage being daily equivalent to about 0.035 mgm. to about 0.05 mgm. ethinyl estradiol combined with about 0.5 mgm. to about 1.0 mgm. norethindrone by oral dosage, for each day for the approximately last 7 days of the luteal phase.

6. The method of claim 3 or claim 4 in which during the luteal phase the dosage of a combined estrogenic active steroid and progestational active steroid comprises:
(i) an initially low dosage equivalent in daily pharmacological activity to about 0.02 mgm. ethinyl estradiol combined with about 0.35 mgm. norethindrone by oral dosage for each day of the early stage of the luteal phase; followed by
(ii) a dosage of greater estrogenic and progestational pharmacological activity than the initial dosage, said dosage being equivalent in daily pharmacological activity to about 0.05 mgm. ethinyl estradiol combined with about 1.0 mgm. to about 2.5 mgm. norethindrone by oral dosage, for each day of the intermediate stage of the luteal phase; followed by
(iii) a dosage during the terminal stage of the luteal phase having a level of estrogenic and progestational pharmacological activity reduced by at least one-half daily from the level of pharmacological activity of the dosage during the intermediate stage.

7. The method of claim 6 in which the daily dosage for each day of the terminal stage of the luteal phase is equivalent in daily pharmacological activity to about 0.02 mgm. ethinyl estradiol combined with about 0.35 mgm. norethindrone by oral dosage.

8. The method of claim 6 in which:
(i) the initial low dosage is administered each day for approximately 4 days;
(ii) the dosage during the intermediate stage is administered for approximately 7 days and is equivalent in daily pharmacological activity to about 0.05 mgm. ethinyl estradiol combined with about 1.0 mgm. norethindrone by oral dosage; and
(iii) the dosage during the terminal stage having a reduced level of pharmacological activity is administered for approximately 3 days.

9. The method of claim 6 in which:
(i) the initial low dosage is administered each day for approximately 2 days;
(ii) the dosage during the intermediate stage is administered for approximately 10 days and is equivalent in daily pharmacological activity to about 0.05 mgm. ethinyl estradiol combined with about 2.5 mgm. norethindrone by oral dosage; and
(iii) the dosage during the terminal stage having a reduced level of pharmacological activity is administered for approximately 2 days.

* * * * *